(12) United States Patent
Bauer et al.

(10) Patent No.: US 9,981,988 B2
(45) Date of Patent: May 29, 2018

(54) POLYMORPHIC FORMS AND CO-CRYSTALS OF A C-MET INHIBITOR

(71) Applicant: AMGEN, INC., Thousand Oaks, CA (US)

(72) Inventors: David Bauer, Sudbury, MA (US); Matthew Bio, Santa Barbara, CA (US); Melanie Cooke, Arlington, MA (US); Katrina W. Copeland, Sudbury, MA (US); Matthew Peterson, Cambridge, MA (US); Michele Potashman, Cambridge, MA (US); Roman Shimanovich, Brighton, MA (US); Helming Tan, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days. days.

(21) Appl. No.: 15/293,511

(22) Filed: Oct. 14, 2016

(65) Prior Publication Data

US 2017/0029443 A1 Feb. 2, 2017

Related U.S. Application Data

(63) Continuation of application No. PCT/US2015/026296, filed on Apr. 17, 2015.

(60) Provisional application No. 61/981,158, filed on Apr. 17, 2014.

(51) Int. Cl.
*C07D 519/00* (2006.01)
*A61K 31/52* (2006.01)
*C07C 55/10* (2006.01)
*C07C 55/12* (2006.01)
*C07C 57/10* (2006.01)
*C07C 57/145* (2006.01)
*C07C 275/02* (2006.01)

(52) U.S. Cl.
CPC ............ *C07D 519/00* (2013.01); *A61K 31/52* (2013.01); *C07C 55/10* (2013.01); *C07C 55/12* (2013.01); *C07C 57/10* (2013.01); *C07C 57/145* (2013.01); *C07C 275/02* (2013.01); *C07B 2200/13* (2013.01)

(58) Field of Classification Search
CPC .................................................. C07D 519/00
See application file for complete search history.

(56) References Cited

U.S. PATENT DOCUMENTS 8,198,448 B2 * 6/2012 Albrecht .............. C07D 471/04
 546/119
9,643,984 B2 * 5/2017 Bio ...................... C07D 471/04

FOREIGN PATENT DOCUMENTS

WO    WO 2014210042 A2 * 12/2014 ........... C07D 471/04

* cited by examiner

*Primary Examiner* — David K O'Dell
(74) *Attorney, Agent, or Firm* — Lucas & Mercanti, LLP

(57) ABSTRACT

Provided herein are novel polymorphic forms and co-crystals of a compound useful in the treatment, prevention, or amelioration of cancer. In particular, the invention provides polymorphs and co-crystals of 6-{(1R)-1-[8-fluoro-6-(1-methyl-1H-pyrazol-4-yl)[1,2,4]triazolo[4,3-a]pyridin-3-yl]ethyl}-3-(2-methoxyethoxy)-1,6-naphthyridin-5(6H)-one, which is an inhibitor of c-Met.

3 Claims, 32 Drawing Sheets

POLYMORPHIC FORMS AND CO-CRYSTALS OF A C-MET INHIBITOR

CROSS-REFERENCE TO RELATED APPLICATION

This application is a by-pass continuation of PCT/US2015/026296, filed Apr. 17, 2015, which claims the benefit under 35 U.S.C. § 119(e) of U.S. Provisional Patent Application Ser. No. 61/981,158 filed Apr. 17, 2014, the disclosure of each of which is incorporated herein by reference.

BACKGROUND OF THE INVENTION

Field of the Invention

The present disclosure relates to novel polymorphic and co-crystal forms of 6-{(1R)-1-[8-fluoro-6-(1-methyl-1H-pyrazol-4-yl)[1,2,4]triazolo[4,3-a]pyridin-3-yl]ethyl}-3-(2-methoxyethoxy)-1,6-naphthyridin-5(6H)-one, methods for their preparation, and methods for their use.

Description of Related Technology

The hepatocyte growth factor receptor ("c-Met") is a unique receptor tyrosine kinase shown to be overexpressed in a variety of malignancies. The ligand for c-Met is hepatocyte growth factor (also known as scatter factor, HGF and SF). Various biological activities have been described for HGF through interaction with c-Met (Hepatocyte Growth Factor-Scatter Factor (HGF-SF) and the c-Met Receptor, Goldberg and Rosen, eds., Birkhauser Verlag-Basel, 67-79 (1993). HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. Overexpression of the c-Met oncogene has also been suggested to play a role in the pathogenesis and progression of thyroid tumors derived from follicular epithelium (Oncogene, 7:2549-2553 (1992)). HGF is a morphogen (Development, 110:1271-1284 (1990); Cell, 66:697-711 (1991)) and a potent angiogenic factor (J. Cell Biol., 119:629-641 (1992)).

Some [1,2,4]triazolo[4,3-a]-pyridine compounds, such as 6-{(1R)-1-[8-fluoro-6-(1-methyl-1H-pyrazol-4-yl)[1,2,4] triazolo[4,3-a]pyridin-3-yl]ethyl}-3-(2-methoxyethoxy)-1, 6-naphthyridin-5(6H)-one, are selective inhibitors of the c-Met receptor, and therefore, are useful in the treatment, prevention, or amelioration of cancer. See, e.g., U.S. Pat. Nos. 8,212,041, 8,217,177, and U.S. Pat. No. 8,198,448, each of which is incorporated herein by reference in its entirety.

SUMMARY

Disclosed herein are novel, free base polymorphic forms and novel, co-crystalline forms of 6-{(1R)-1-[8-fluoro-6-(1-methyl-1H-pyrazol-4-yl)[1,2,4]triazolo[4,3-a]pyridin-3-yl] ethyl}-3-(2-methoxyethoxy)-1,6-naphthyridin-5(6H)-one ("Compound M"), which is a selective inhibitor of the c-Met receptor, and useful in the treatment, prevention, or amelioration of cancer:

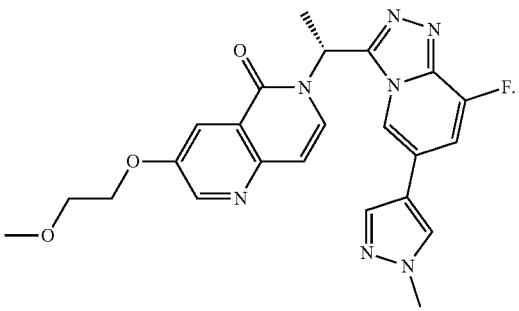 [SMILES: COCCOc1cnc2ccn([C@H](C)c3nnc4c(F)cc(-c5cnn(C)c5)cn34)c(=O)c2c1]

In one aspect, there is a free base monohydrate form of Compound M. In embodiments, the free base monohydrate form of Compound M can be crystalline. The free base monohydrate form of Compound M can be characterized by an X-ray powder diffraction pattern comprising peaks at about 6.6, 7.9, 14.5, 15.1, 15.8 and 22.2±0.2° 2θ using Cu Kα radiation. The free base monohydrate form of Compound M can be formed by, for example: (a) preparing a slurry comprising Compound M in an organic solvent that is free or substantially free of each or all of DMSO, propylene glycol, PEG 400, and acetone, wherein the slurry comprises at least about 0.25 water activity, and isolating the resulting solid; or, (b) exposing an anhydrous form I of Compound M to at least about 25% relative humidity.

In another aspect, there is a free base acetone solvate form of Compound M. In embodiments, the free base acetone solvate form of Compound M can include about a 1:1 molar ratio of acetone to Compound M. The free base acetone solvate form of Compound M can be characterized by an X-ray powder diffraction pattern comprising peaks at about 7.2, 15.5, 17.1, 22.0, and 23.1±0.2° 2θ using Cu Kα radiation. In embodiments, the free base acetone solvate form of Compound M can be formed by preparing a slurry of the free base monohydrate form of Compound M in acetone, and isolating the resulting solid.

In yet another aspect there is a free base dimethylsulfoxide (DMSO) hemisolvate form of Compound M. In embodiments, the free base DMSO hemisolvate form of Compound M can include about a 1:2 molar ratio of DMSO to Compound M. The free base DMSO hemisolvate form of Compound M can be characterized by an X-ray powder diffraction pattern comprising peaks at about 7.3, 13.9, 14.3, 16.2, and 27.8±0.2° 2θ using Cu Kα radiation. In embodiments, the free base DMSO hemisolvate form of Compound M can be formed by preparing a slurry of the free base monohydrate form of Compound M in DMSO, and isolating the resulting solid.

In still another aspect, there is a free base anhydrous form of Compound M. In embodiments, the free base anhydrous form of Compound M can be crystalline. The free base anhydrous form of Compound M can be characterized by an X-ray powder diffraction pattern comprising peaks at about 7.2, 8.2, 14.7, 16.4, and 23.1±0.2° 2θ using Cu Kα radiation, and/or a hydration onset in a range of 24% to 31% relative humidity at a temperature in a range of 25° C. to 45° C. In these embodiments, the free base anhydrous form is referred to herein as the free base "anhydrous I" form of Compound M. The free base anhydrous I form of Compound M can be formed by, for example: (a) heating the free base monohydrate form of Compound M to a temperature greater than 45° C.; or (b) subjecting the free base monohydrate form of Compound M to a relative humidity of less than about 15%; or (c) preparing a slurry of the free base monohydrate form of Compound M in an organic solvent that is not DMSO or acetone, wherein the slurry comprises less than about 0.15 water activity, and isolating the resulting solid.

The free base anhydrous form of Compound M can be characterized by an X-ray powder diffraction pattern comprising peaks at about 7.6, 8.9, 11.5, 11.9, and 13.4±0.2° 2θ using Cu Kα radiation. In these embodiments, the free base anhydrous form is referred to herein as the free base "anhydrous II" form of Compound M." In embodiments, the free base anhydrous II form of Compound M can be formed by desiccating a solid powder of the acetone solvate form of Compound M, and rehydrating the desiccated solid at no less than about 30% relative humidity.

In another aspect, there is a free base amorphous form of Compound M. The free base anhydrous form of Compound M can be characterized by, for example, an X-ray powder diffraction spectrum substantially as appears in FIG. 6A and/or a differential scanning calorimetry thermograph substantially as appears in FIG. 6B. In embodiments, the free base amorphous form of Compound M can be formed by evaporating a crude reaction mixture of Compound M onto a substrate, purifying the crude reaction mixture via flash chromatography, collecting the resulting solution, and evaporating the solvent.

In still another aspect, there is a co-crystal form of Compound M. In embodiments, the co-crystal can include a coformer selected from the group consisting of phosphoric acid, maleic acid, succinic acid, sorbic acid, glutaric acid, and urea.

In embodiments wherein the coformer is phosphoric acid, the co-crystal form can include about a 1:1 molar ratio of phosphoric acid to Compound M, and can be characterized by an X-ray powder diffraction pattern comprising peaks at about 9.4, 12.7, 17.3, 21.1, and 23.1±0.2° 2θ using Cu Kα radiation.

In embodiments wherein the coformer is maleic acid, the co-crystal form can include about a 1:1 molar ratio of maleic acid to Compound M, and can be characterized by an X-ray powder diffraction pattern comprising peaks at about 10.0, 12.6, 17.5, 21.1, and 23.3±0.2° 2θ using Cu Kα radiation.

In embodiments wherein the coformer is succinic acid, the co-crystal form can include about a 2:1 molar ratio of succinic acid to Compound M, and can be characterized by an X-ray powder diffraction pattern comprising peaks at about 5.3, 10.7, 12.5, 13.7, and 26.8±0.2° 2θ using Cu Kα radiation.

In embodiments wherein the coformer is sorbic acid, the co-crystal form can include about a 2:1 molar ratio of sorbic acid to Compound M, and can be characterized by an X-ray powder diffraction pattern comprising peaks at about 7.9, 8.5, 9.7, 17.2, and 22.5±0.2° 2θ using Cu Kα radiation.

In embodiments wherein the coformer is glutaric acid, the co-crystal form can include about a 2:1 molar ratio of glutaric acid to Compound M, and can be characterized by an X-ray powder diffraction pattern comprising peaks at about 6.7, 7.0, 10.7, 15.3, and 21.0±0.2° 2θ using Cu Kα radiation.

In embodiments wherein the coformer is urea, the co-crystal form can include about a 1:1 molar ratio of urea to Compound M, and can be characterized by an X-ray powder diffraction pattern comprising peaks at about 8.1, 8.9, 16.1, 21.0, and 28.4±0.2° 2θ using Cu Kα radiation.

Another aspect of the disclosure is use or administration of any one of the compounds described herein for selective inhibition of the c-Met receptor, and optionally for use in the treatment, prevention, or amelioration of cancer.

For the compositions and methods described herein, optional features, including but not limited to components, compositional ranges thereof, substituents, conditions, and steps, are contemplated to be selected from the various aspects, embodiments, and examples provided herein.

Further aspects and advantages will be apparent to those of ordinary skill in the art from a review of the following detailed description, taken in conjunction with the drawings. While the polymorphic forms and co-crystalline forms of Compound M are susceptible of embodiments in various forms, the description hereafter includes specific embodiments with the understanding that the disclosure is illustrative, and is not intended to limit the invention to the specific embodiments described herein.

DETAILED DESCRIPTION

Figure 1A:
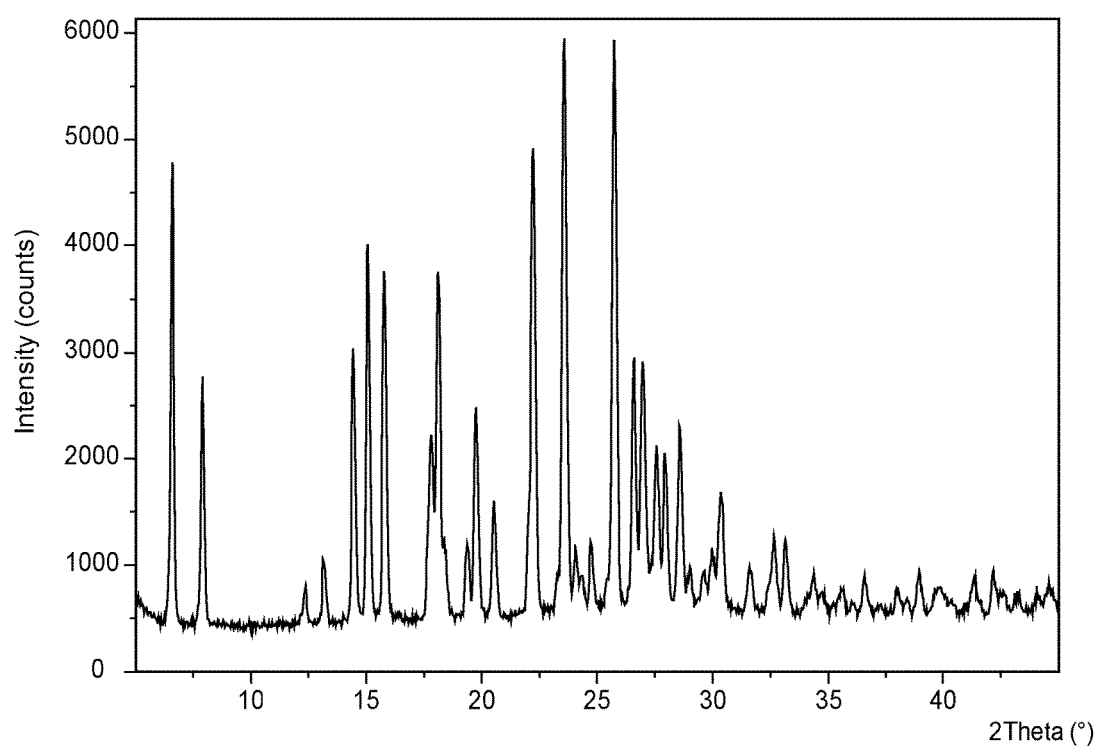
FIG. 1A depicts an X-ray powder diffraction (XRPD) pattern of the free base monohydrate form of Compound M.

Provided herein are novel, free base polymorphic forms and novel, co-crystalline forms of 6-{(1R)-1-[8-fluoro-6-(1-methyl-1H-pyrazol-4-yl)[1,2,4]triazolo[4,3-a]pyridin-3-yl]ethyl}-3-(2-methoxyethoxy)-1,6-naphthyridin-5(6H)-one ("Compound M"):

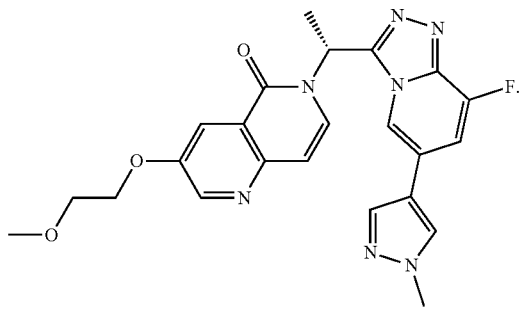 [SMILES: COCCOc1cnc2ccn([C@H](C)c3nnc4c(F)cc(-c5cnn(C)c5)cn34)c(=O)c2c1]

Each polymorph and co-crystal described herein can be made from Compound M. Methods and processes relating to the preparation of Compound M are disclosed in co-pending U.S. Provisional Patent application Ser. No. 61/838,856, which is incorporated herein by reference in its entirety.

The polymorphic forms and co-crystalline forms of Compound M, their methods of preparation, and their methods of use are contemplated to include embodiments including any combination of one or more of the additional optional elements, features, and steps further described below (including those shown in the figures), unless stated otherwise.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "comprising" indicates the potential inclusion of other agents, elements, steps, or features, in addition to those specified.

As used herein, the term "polymorphs" or "polymorphic forms" refers to crystal forms of the same molecule. Different polymorphic forms of a molecule have different physical properties as a result of the arrangement or conformation of the molecules in the crystal lattice. Some of the different physical properties include melting temperature, heat of fusion, solubility, dissolution rate, and/or or vibrational spectra. The physical form of a particular compound is particularly important when the compound is used in a pharmaceutical formulation because different solid forms of a compound result in different properties of the drug product.

Polymorphs of a molecule can be obtained by a number of methods, as shown in the art, such as, for example, melt recrystallization, melt cooling, solvent recrystallization, desolvation, rapid evaporation, rapid cooling, slow cooling, vapor diffusion, and sublimation. Techniques for characterizing a polymorph include X-ray powder diffraction (XRPD), single crystal X-ray diffraction (XRD), differential scanning calorimetry (DSC), vibrational spectroscopy (e.g., IR and Raman spectroscopy), solid state nuclear magnetic resonance (ssNMR), hot stage optical microscopy, scanning electron microscopy (SEM), electron crystallography and quantitative analysis, particle size analysis (PSA), surface area analysis, solubility studies, and dissolution studies.

As used herein, the term "solvate" refers to a crystal form of a substance that contains an association between a substrate and a solvent.

As used herein, the term "hemisolvate" refers to a solvate containing one molecule of solvent per two molecules of the substrate.

As used herein, the term "hydrate" refers to a solvate wherein the solvent is water.

As used herein, the term "monohydrate" refers a hydrate that contains one molecule of water per one molecule of the substrate.

As used herein, the term "crystalline" refers to a solid in which the constituent atoms, molecules, or ions are arranged in a regularly ordered, repeating pattern in three dimensions.

As used herein, the term "co-crystal" refers to a crystalline material that comprises two or more unique components held together by weak interactions (e.g., hydrogen bonding, pi-stacking, guest-host complexation, and/or van der Waals forces), wherein each component is a solid under ambient conditions when in its pure form. Each co-crystal contains distinctive physical characteristics, such as structure, melting point, and heat of fusion. The term "co-crystal" does not include salts, which are distinguished by proton transfer to result in an electrostatic linkage between oppositely charged ions, or solvates, which are associations of substrates with solvents (i.e., liquids at ambient temperature) from which they are crystallized, as defined above.

As used herein, the term "amorphous" refers to a solid that lacks the long-range order of a crystal.

If there is a discrepancy between a depicted chemical structure and a chemical name given to that structure, the depicted chemical structure controls.

Free Base Monohydrate Form of Compound M

In one aspect, the disclosure provides a free base monohydrate form of Compound M. In various embodiments of this aspect, the free base monohydrate form of Compound M is crystalline. Embodiments of the free base monohydrate form of Compound M can be characterized by one or more of the parameters described in further detail below.

The free base monohydrate form of Compound M has an aqueous solubility of about 0.26 mg/mL at a pH in a range of about 4 to about 7 and a temperature of about 20° C. to about 25° C. The solubility of the free base monohydrate form of Compound M increases slightly at acidic pH, increases significantly in the presence of surfactants, and decreases slightly at higher ionic strength. For example, the free base monohydrate form of Compound A has a solubility of 0.35 mg/mL at pH 2, 1.44 mg/mL in 0.25% (w/v) SDS, and 0.18 mg/mL in PBS, as described in Example 1. The free base monohydrate form of Compound M is soluble in organic solvents, such as, for example, methanol, ethanol, isopropanol, acetonitrile, ethyl acetate, methyl ethyl ketone, and DMSO/water mixtures, as described in Example 3.

Figure 1B:
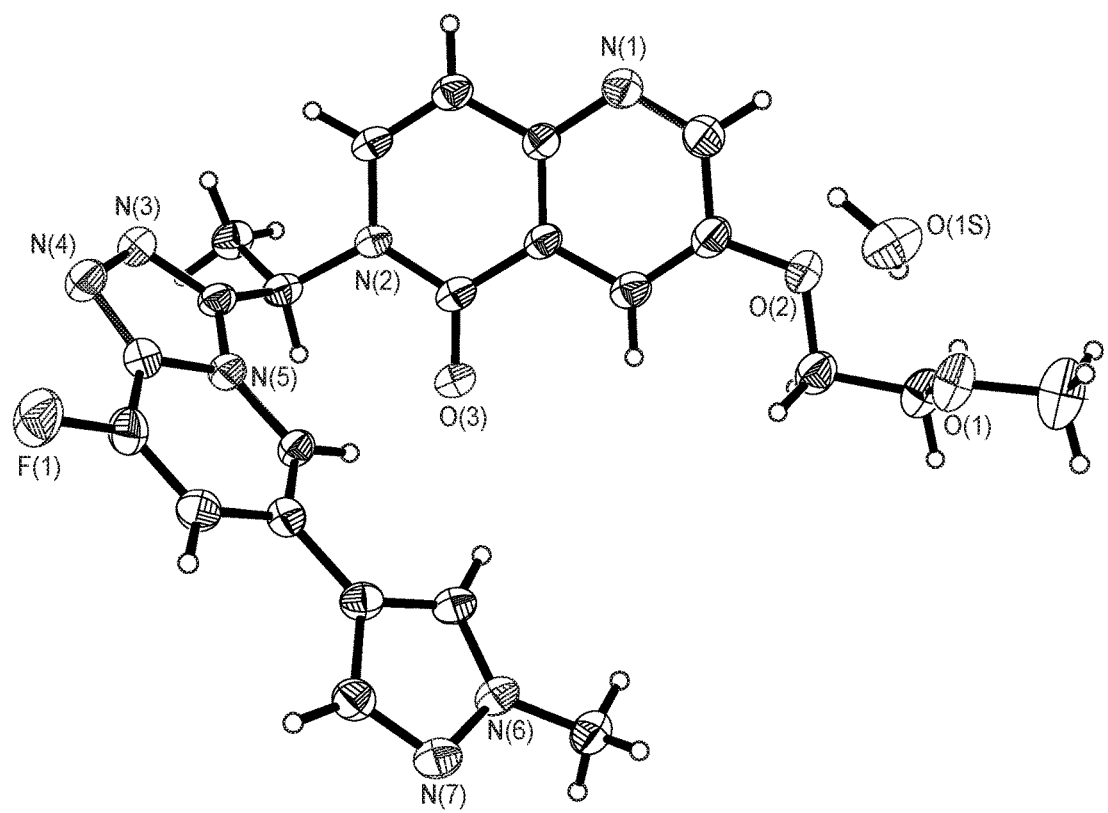
FIG. 1B depicts a single crystal X-ray diffraction (XRD) structure of the free base monohydrate form of Compound M.
Figure 1C:
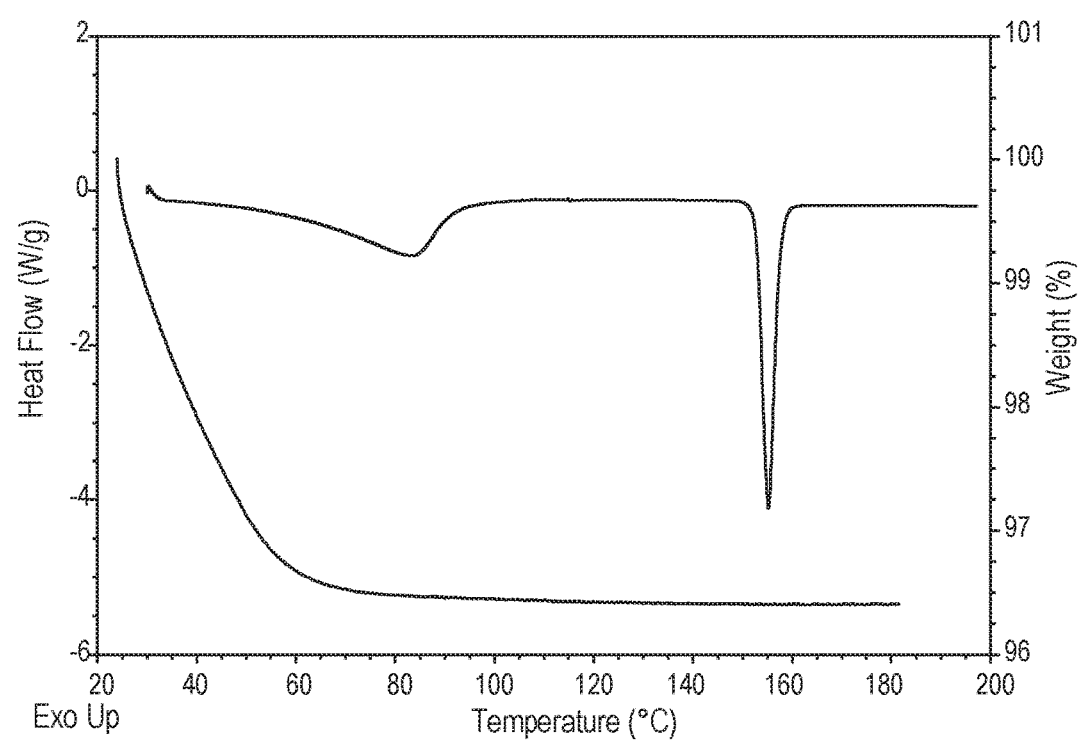
FIG. 1C depicts a differential scanning calorimetry (DSC) thermograph (top trace) and a thermogravimetric analysis (TGA) trace (bottom trace) of the free base monohydrate form of Compound M when the sample is heated from 25° C. at a rate of 10° C./min.
Figure 1D:
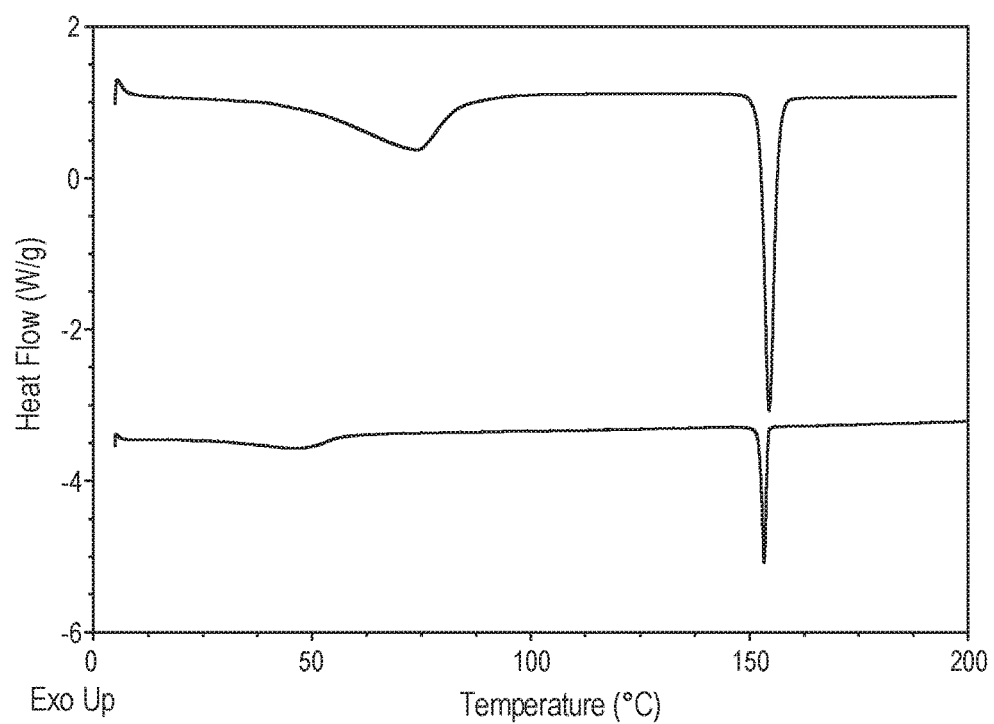
FIG. 1D depicts a DSC thermograph of the free base monohydrate form of Compound M when the sample is heated from 5° C. at a rate of 10° C./min (top trace) and 2° C./min (bottom trace).
Figure 1E:
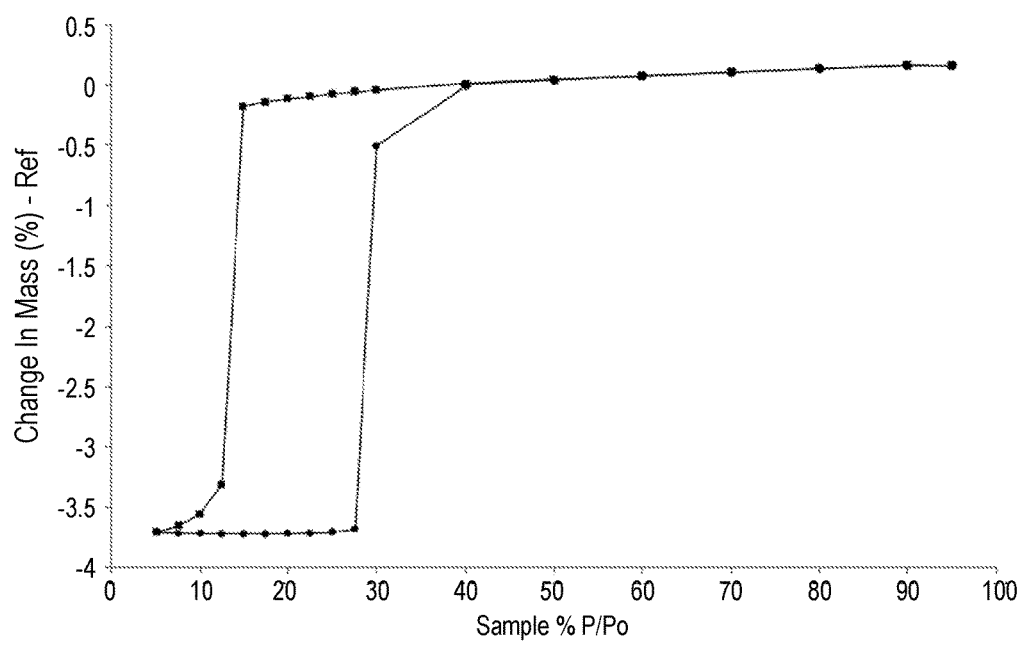
FIG. 1E depicts an isotherm plot of the free base monohydrate form of Compound M obtained from a dynamic vapor sorption experiment.

The free base monohydrate from of Compound M is non-hygroscopic. For example, when subjected to dynamic vapor sorption, as described in the Methods section, the free base monohydrate form of Compound M demonstrated a total weight gain of about 0.2 wt. % between about 40% and about 90% relative humidity, as depicted in FIG. 1E.

The free base monohydrate form of Compound M is stable under accelerated stability testing conditions, when subjected to chemical stress, and when subjected for photostress. For example, the free base monohydrate form of Compound M remains in substantially the same physical form over 12 weeks at 25° C. and 60% relative humidity or at 40° C. and 75% relative humidity. Further still, the free base monohydrate form of Compound M exhibits low levels of degradation under photostress conditions (1×ICH dose for UV and vis light exposure), such as 0.2% under visible conditions and 0.4% under UV conditions, as described in Example 4. In embodiments, the free base monohydrate form of Compound M can be characterized by an X-ray powder diffraction pattern, obtained as set forth in the Methods section, having peaks at about 6.6, 7.9, 14.5, 15.1, 15.8 and 22.2±0.2° 2θ using Cu Kα radiation. The free base monohydrate form of Compound M optionally can be further characterized by an X-ray powder diffraction pattern having additional peaks at about 12.4, 13.2, 17.8, 18.1, 19.4, 19.7, 20.5, 23.6, 25.7±0.2° 2θ using Cu Kα radiation. In embodiments, the free base monohydrate form of Compound M can be characterized by an X-ray powder diffraction pattern substantially as depicted in FIG. 1A.

In one embodiment, the free base monohydrate form of Compound M can be characterized by a single crystal X-ray diffraction (XRD) structure, obtained as set forth in the Methods section, wherein the free base monohydrate form comprises a monoclinic space group of $P2_1$ and unit cell parameters of about a=12.2708(6) Å, b=6.8666(4) Å, c=14.6871(9) Å, and β=113.580(4)°. The free base monohydrate form of Compound M optionally can be further characterized by the XRD parameters in the table, below, and as represented in FIG. 1B.

| Wavelength | 1.54178 Å |
|---|---|
| Crystal system | Monoclinic |
| Space group | $P2_1$ |
| Unit cell dimensions | a = 12.2708(6) Å |
| | α = γ = 90° |
| | b = 6.8666(4) Å |
| | β = 113.580(4)° |
| | c = 14.6871(9) Å |
| Volume | 1134.19(11) Å$^3$ |
| Z | 2 |
| Density (calculated) | 1.410 Mg/m$^3$ |
| Flack parameter | 0.1(3) |

The free base monohydrate form of Compound M can be characterized by its dehydration onset obtained by, for example, differential scanning calorimetry (DSC), hot stage microscopy, and dynamic vapor sorption (DVS) methods.

DSC thermographs were obtained as set forth in the Methods section. The dehydration of the free base monohydrate form of Compound M is a kinetic event that is influenced by experimental parameters. Thus, in embodiments, the free base monohydrate form of Compound M can be characterized by a DSC thermograph having a dehydration endotherm with an onset in a range of about 40° C. to about 55° C. when the free base monohydrate form is heated in an open aluminum pan. For example, in embodiments wherein the free base monohydrate of Compound M is heated from about 25° C. at a rate of about 10° C./min, the free base monohydrate of Compound M can be characterized by a DSC thermograph having a dehydration endotherm with an onset of about 55° C. and a peak at about 84° C., as shown in FIG. 1C (top trace). In embodiments wherein the free base monohydrate of Compound M is heated from 5° C. at a rate of about 10° C./min, the free base monohydrate of Compound M can be characterized by a DSC thermograph having a dehydration endotherm with an onset of about 44° C. and a peak at about 74° C., as shown in FIG. 1D (top trace). In embodiments wherein the free base monohydrate of Compound M is heated from 5° C. at a rate of about 2° C./min, the free base monohydrate of Compound M can be characterized by a DSC thermograph having a dehydration endotherm with an onset of about 26° C. and a peak at about 46° C., as shown in FIG. ID (bottom trace). In embodiments, the free base monohydrate form of Compound M can be characterized by a DSC thermograph substantially as depicted in FIG. 1C (top trace) and/or 1D.

In embodiments, the free base monohydrate form of Compound M can be characterized by a dehydration onset, obtained via DVS experiments as set forth in the Methods section, in a range of about 15% to about 25% relative humidity at a temperature in a range of about 25° C. to about 45° C.

The free base monohydrate form of Compound M can be characterized by thermogravimetric analysis (TGA). The dehydration of the free base monohydrate form of Compound M is a kinetic event that is influenced by experimental parameters. TGA thermographs were obtained as set forth in the Methods section. Thus, in embodiments, the free base monohydrate form of Compound M can be characterized by a weight loss in a range of about 3.0% to about 3.8%, with an onset temperature in a range of about 20° C. to about 25° C. For example, the free base monohydrate from of Compound M can be characterized by a weight loss of about 3.6%, with an onset at about 25° C., as depicted in FIG. 1C (bottom trace). In embodiments, the free base monohydrate form of Compound M can be characterized by a TGA trace substantially as depicted in FIG. 1C (bottom trace).

Figure 1F:
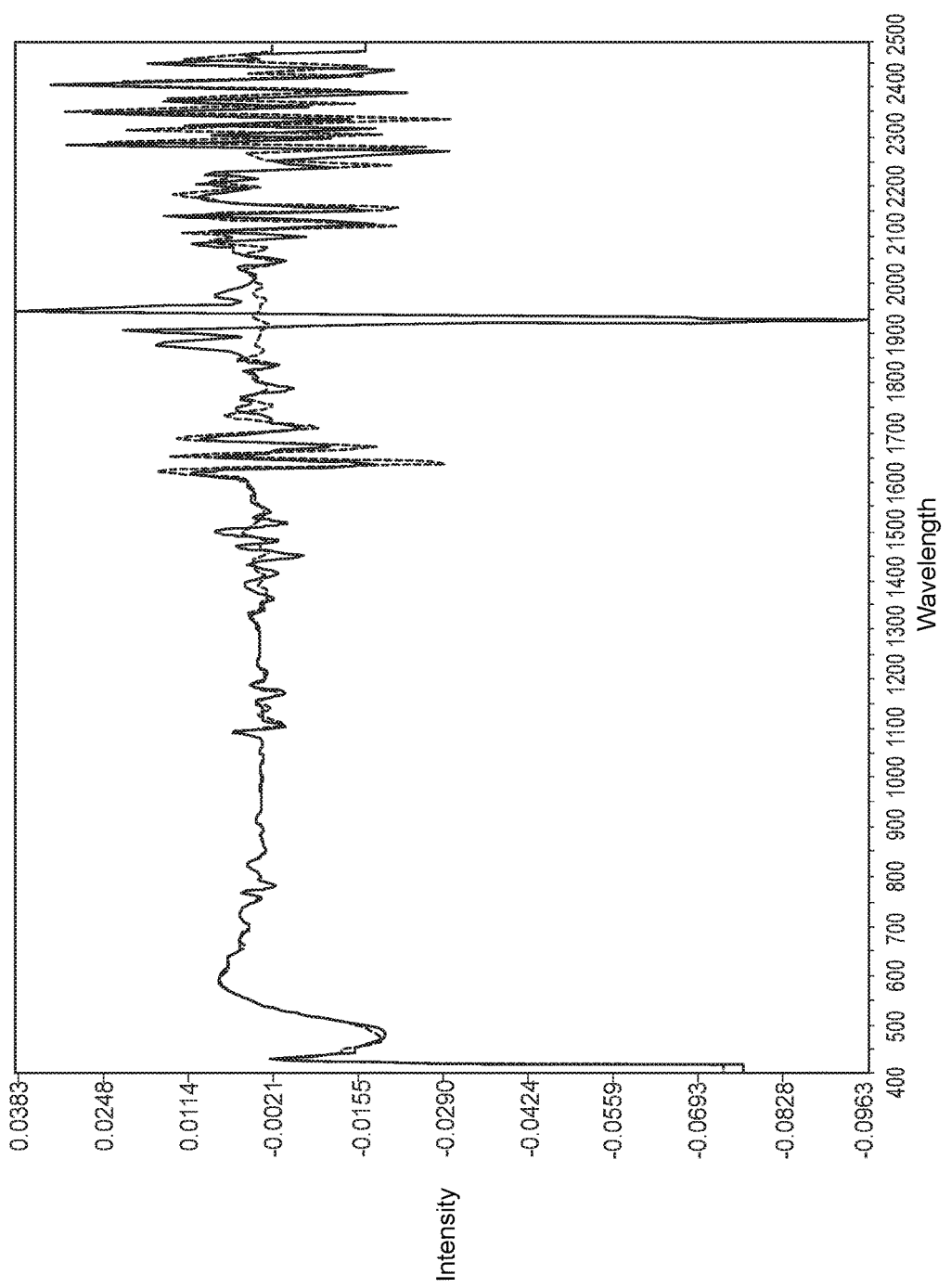
FIG. 1F depicts a near-IR spectrum of the free base monohydrate form of Compound M (solid line) and the anhydrous I form of Compound M (dashed line).

The free base monohydrate form of Compound M can be characterized by near-IR, as set forth in the Methods section. In embodiments, the free base monohydrate form of Compound M can be characterized by a near-IR spectrum having a water band at 1850-2000 nm. For example, the free base monohydrate form of Compound M can be characterized by a near-IR spectrum substantially as depicted in FIG. 1F (solid line).

The free base monohydrate form of Compound M can be formed in a variety of ways. In one type of embodiment, the free base monohydrate form of Compound M can be formed by preparing a slurry containing Compound M in an organic solvent that is free or substantially free of each or all of DMSO, propylene glycol, PEG 400, and acetone, wherein the slurry comprises at least about 0.25 water activity, and then isolating the resulting solid. For example, the free base monohydrate form of Compound M can be formed by preparing a slurry containing Compound M in acetonitrile/water, and then isolating the resulting substrate. In another type of embodiment, the free base monohydrate form of Compound M can be formed by exposing a free base anhydrous form I of Compound M to at least about 25% relative humidity.

Free Base Anhydrous Form of Compound M

In another aspect, the disclosure provides a free base anhydrous form of Compound M.

In various embodiments, the free base anhydrous form of Compound M can be crystalline. The free base anhydrous form of Compound M can be characterized by one or more of the parameters described below.

Figure 2A:
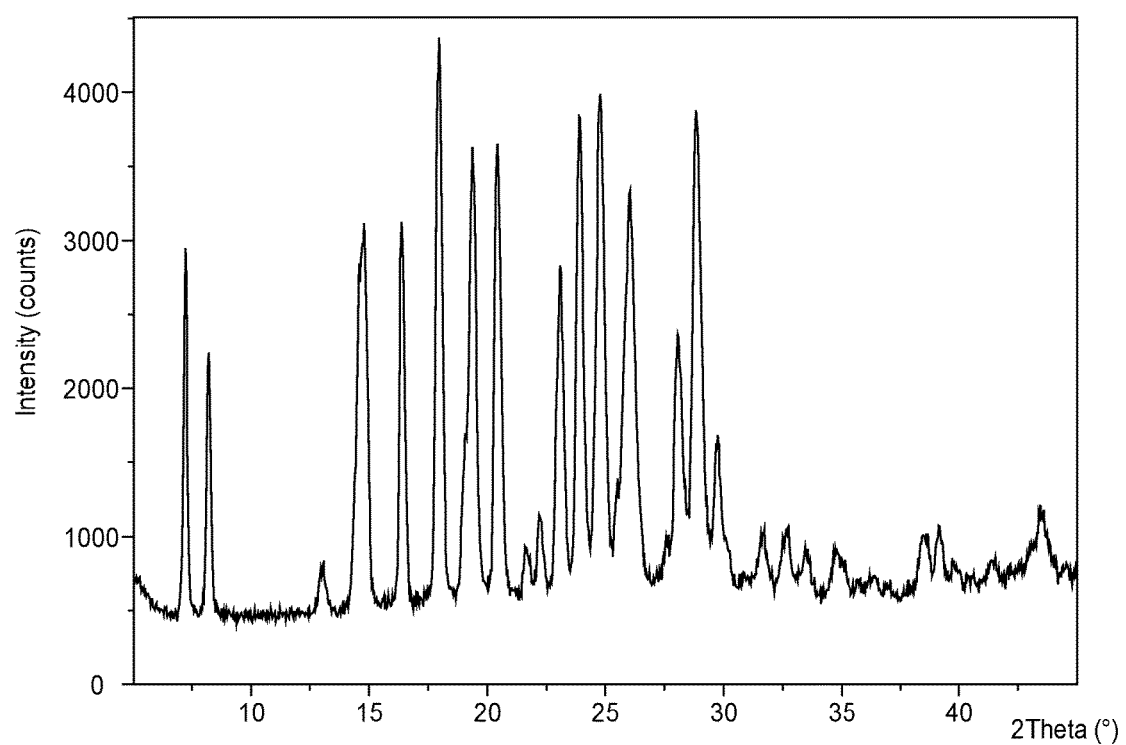
FIG. 2A depicts an XRPD pattern of the free base anhydrous I form of Compound M.

The free base anhydrous form of Compound M can be characterized by an X-ray powder diffraction pattern, obtained as set forth in the Methods section, having peaks at about 7.2, 8.2, 14.7, 16.4, and 23.1±0.2° 2θ using Cu Kα radiation. When the free base anhydrous form of Compound M is characterized by the aforementioned XRPD peaks, then the form is referred to herein as the free base "anhydrous I" form of Compound M. The free base anhydrous I form of Compound M optionally can be further characterized by an X-ray powder diffraction pattern having additional peaks at about 13.0, 17.9, 19.4, 20.4, 23.9, 24.8, 26.1, 28.1, 28.9, 29.8±0.2° 2θ using Cu Kα radiation. In embodiments, the free base anhydrous I form of Compound M can be characterized by an X-ray powder diffraction pattern substantially as depicted in FIG. 2A.

Figure 2B:
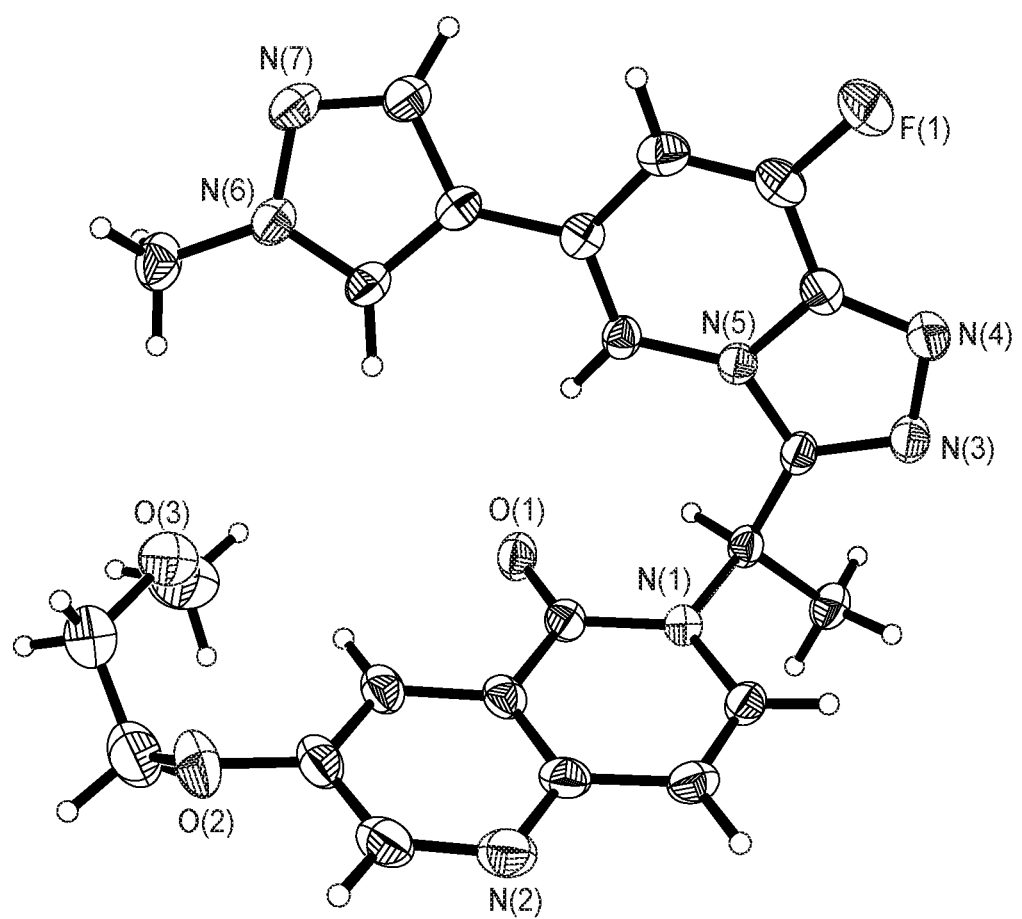
FIG. 2B depicts a single crystal XRD structure of the free base anhydrous I form of Compound M.

In one embodiment, the free base anhydrous I form of Compound M can be characterized by a single crystal XRD structure, obtained as set forth in the Methods section, wherein the free base anhydrous form comprises a monoclinic space group of P2$_1$ and unit cell parameters of about a=12.2395(2) Å, b=7.10130(10) Å, c=13.7225(2) Å, and β=116.1010(10)°. The free base anhydrous I form of Compound M optionally can be further characterized by the XRD parameters in the table, below, and as represented in FIG. 2B.

| Crystal system | Monoclinic |
|---|---|
| Space group | P2$_1$ |
| Unit cell dimensions | a = 12.2395(2) Å; α = 90° |
| | b = 7.10130(10) Å; β = 116.1010(10)° |
| | c = 13.7225(2) Å; γ = 90° |
| Volume | 1071.08(3) Å$^3$ |
| Z | 2 |
| Density (calculated) | 1.437 mg/m$^3$ |

Figure 2C:
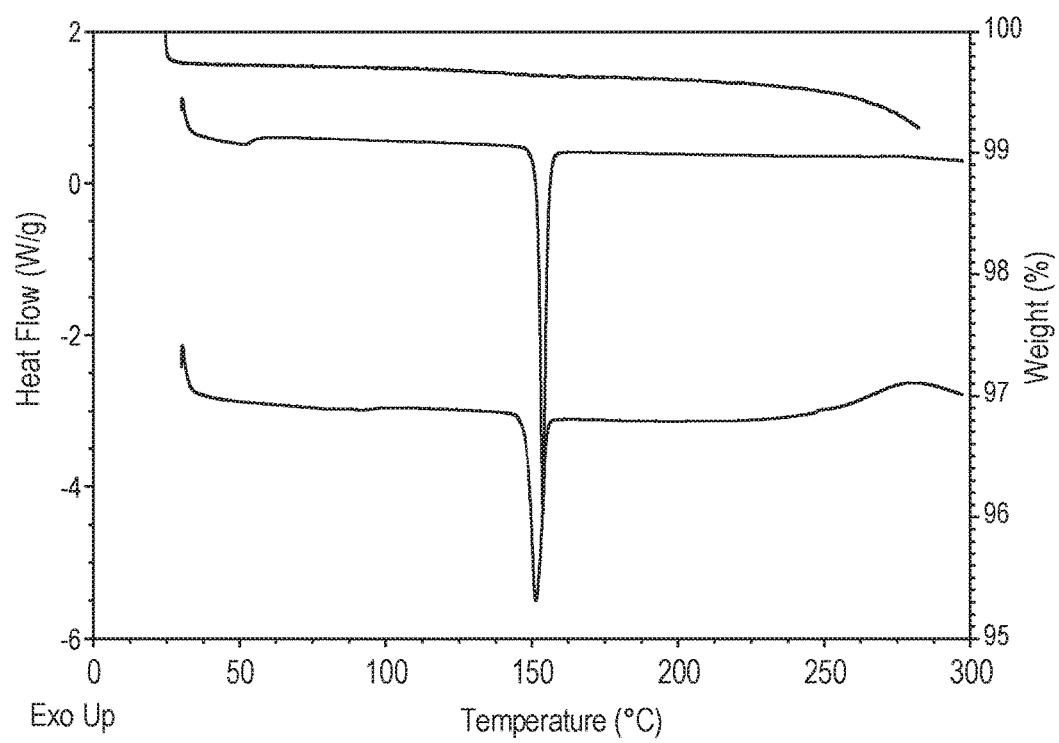
FIG. 2C depicts a TGA trace (top trace), a standard DSC thermograph (middle trace), and a hermetic DSC thermograph (bottom trace) of the anhydrous I form of Compound M when the sample is heated from 25° C. at a rate of 10° C./min.

The free base anhydrous I form of Compound M can be characterized by DSC thermographs, obtained as set forth in the Methods section. In embodiments, the free base anhydrous I form of Compound M can be characterized by a DSC thermograph having a melt endotherm with an onset in a range of about 151° C. to about 153° C. when the anhydrous I form is heated in an open aluminum pan. For example, when embodiments of the free base anhydrous I form of Compound M are heated from about 25° C. at a rate of about 10° C./min, the free base anhydrous I form of Compound M can be characterized by a DSC thermograph having a melt endotherm with an onset of about 152° C., as depicted in FIG. 2C (middle trace). In embodiments, the free base anhydrous I form of Compound M can be characterized by a DSC thermograph substantially as depicted in FIG. 2C (middle trace).

In embodiments, the free base anhydrous I form of Compound M can be characterized by TGA. TGA thermographs were obtained as set forth in the Methods section. Thus, in embodiments, the free base anhydrous I form of Compound M can be characterized by substantially no weight loss, as depicted in FIG. 2C (top trace).

In embodiments, the free base anhydrous I form of Compound M can be characterized by a hydration onset, obtained using moisture sorption experiments as described in the Methods section, in a range of 24% to 31% relative humidity at a temperature in a range of 25° C. to 45° C.

The free base anhydrous I form of Compound M can be characterized by near-IR, as set forth in the Methods section. Thus, in some embodiments, the free base anhydrous I form of Compound M can be characterized by a near-IR spectrum having no water band at 1850-2000 nm. For example, the free base anhydrous I form of Compound M can be characterized by a near-IR spectrum substantially as depicted in FIG. 1F (dashed line).

The free base anhydrous I form of Compound M can be formed in a variety of ways. In one type of embodiment, the free base anhydrous I form of Compound M is prepared by heating the free base monohydrate form of Compound M to a temperature greater than 45° C. For example, the free base anhydrous I form of Compound I can be prepared by heating the free base monohydrate form of Compound M to at least about 45° C. at a relative humidity below 30%.

In another type of embodiment, the free base anhydrous I form of Compound M is prepared by subjecting the free base monohydrate form of Compound M to a relative humidity of less than about 15%. For example, the free base anhydrous I form of Compound M can be prepared by subjecting the free base monohydrate form of Compound M to a relative humidity of less than about 15% at a temperature in a range of about 25° C. to about 45° C.

In yet another type of embodiment, the free base anhydrous I form of Compound M is formed by preparing a slurry of the free base monohydrate form of Compound M in an organic solvent that is not DMSO or acetone, wherein the slurry comprises less than 0.15 water activity, and isolating the resulting solid.

Figure 3A:
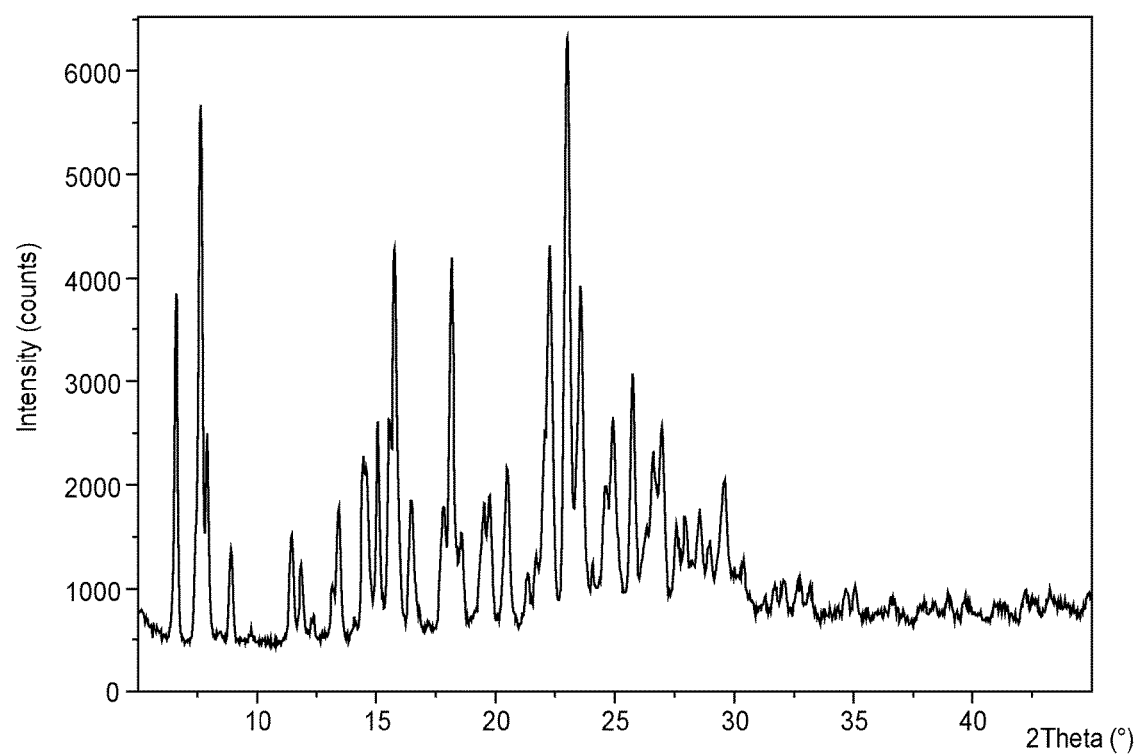
FIG. 3A depicts an XRPD pattern of a mixture of the free base anhydrous I and anhydrous II forms of Compound M.

The free base anhydrous form of Compound M can be characterized by an X-ray powder diffraction pattern, obtained as set forth in the Methods section, having peaks at about 7.6, 8.9, 11.5, 11.9, and 13.4±0.2° 2θ using Cu Kα radiation. When the free base anhydrous form of Compound M is characterized by the aforementioned XRPD peaks, then the form is referred to herein as the free base "anhydrous II" form of Compound M. The free base anhydrous II form of Compound M optionally can be further characterized by an X-ray powder diffraction pattern having additional peaks at about 15.5, 16.5, 23.0, and 24.9±0.2° 2θ using Cu Kα radiation. A XRPD pattern depicting a mixture of the free base anhydrous I and anhydrous II forms of Compound M is shown in FIG. 3A.

Figure 3B:
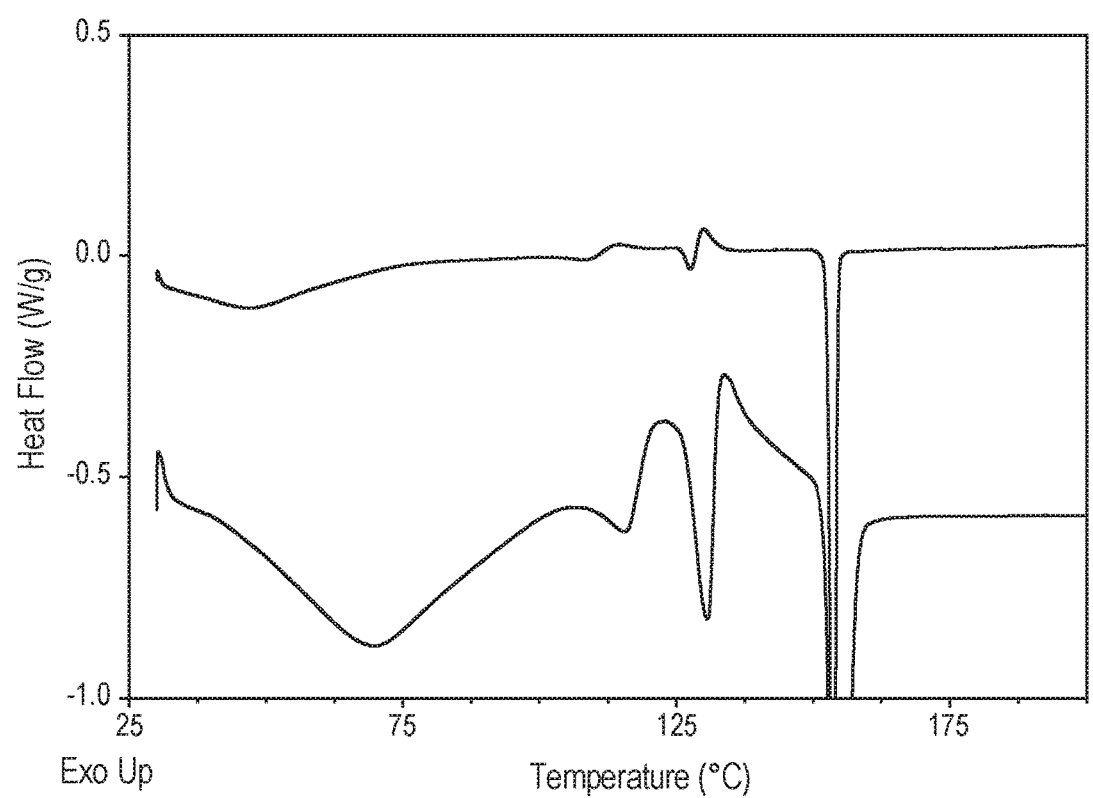
FIG. 3B depicts a DSC thermograph of the free base anhydrous II form of Compound M when the sample is heated from 25° C. at a rate of 2° C./min (top trace) and 10° C./min (bottom trace).

The free base anhydrous II form of Compound M can be characterized by DSC, as set forth in the Methods section. In embodiments, the free base anhydrous II form of Compound M can be characterized by a DSC thermograph having an endothermic event at a temperature in a range of about 100° C. to about 120° C. when the anhydrous II form of Compound M is heated in an open aluminum pan. For example, when embodiments of the free base anhydrous form II of Compound M are heated from about 25° C. at a rate of about 10° C./min, the free base anhydrous II form of Compound M can be characterized by a DSC thermography having an endothermic event with an onset of about 110° C. and a peak at about 115° C., as shown in FIG. 3B (bottom trace). In embodiments, the free base anhydrous II form of Compound M can be characterized by a DSC thermograph substantially as depicted in FIG. 3B (bottom trace).

The free base anhydrous II form of Compound M can be formed in a variety of ways. In one type of embodiment, the free base anhydrous II form of Compound M can be prepared by desiccating a solid powder of the acetone solvate form of Compound M, and rehydrating the desiccated solid at no less than about 30% relative humidity.

Acetone Solvate Form of Compound M

In another aspect, the disclosure provides an acetone solvate form of Compound M. The acetone solvate form of Compound M can be characterized by one or more of the parameters described below.

In embodiments, the acetone solvate form of Compound M can include about a 1:1 molar ratio of acetone to Compound M.

Figure 4A:
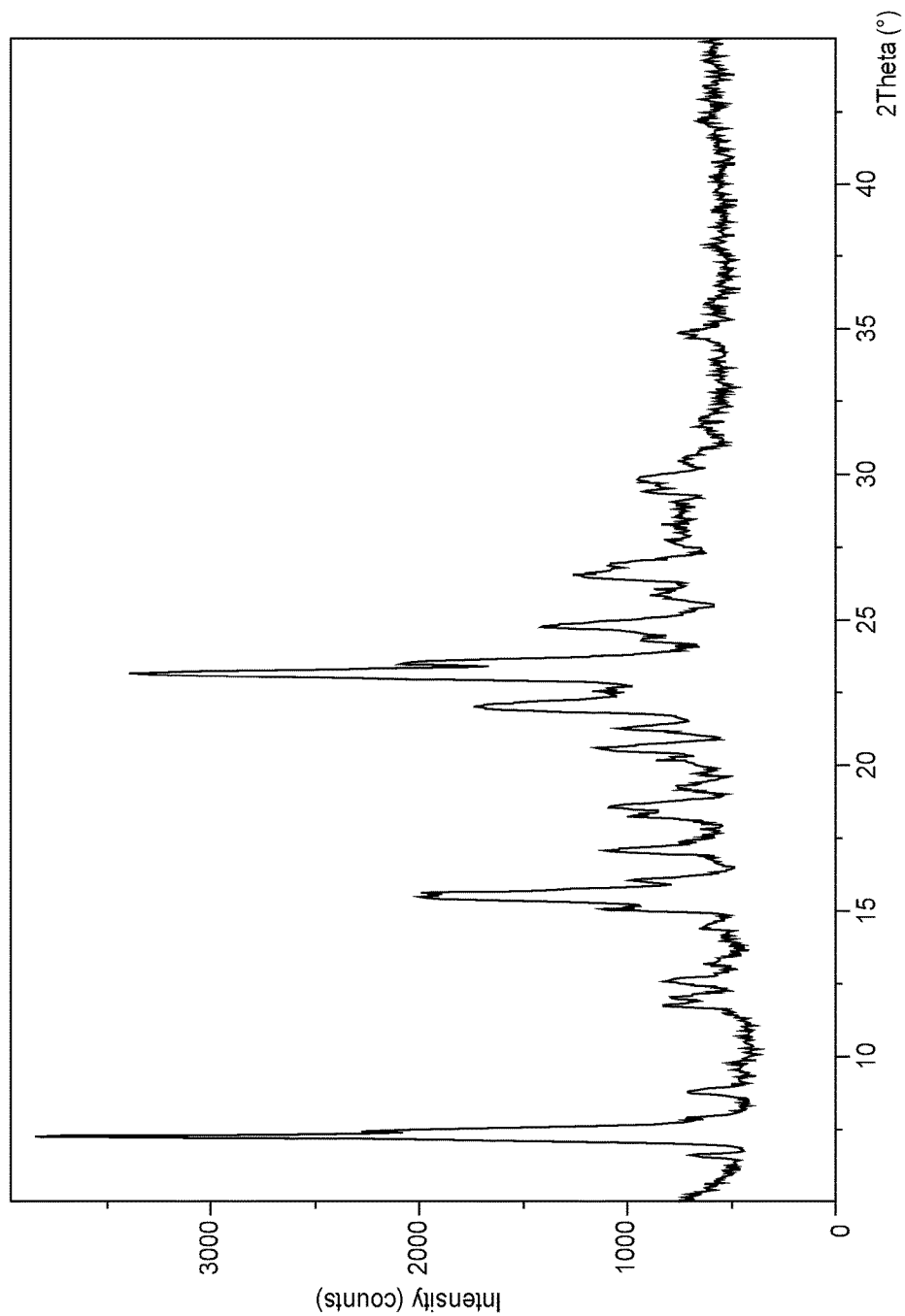
FIG. 4A depicts an XRPD pattern of the free base acetone solvate form of Compound M.

The free base acetone solvate form of Compound M can be characterized by an X-ray powder diffraction pattern, obtained as set forth in the Methods section, having peaks at about 7.2, 15.5, 17.1, 22.0, and 23.1±0.2° 2θ using Cu Kα radiation. The free base acetone solvate form of Compound M optionally can be further characterized by an X-ray powder diffraction pattern having additional peaks at about 20.6 and 24.8±0.2° 2θ using Cu Kα radiation. In embodiments, the free base acetone solvate form of Compound M can be characterized by an X-ray powder diffraction pattern substantially as depicted in FIG. 4A.

Figure 4B:
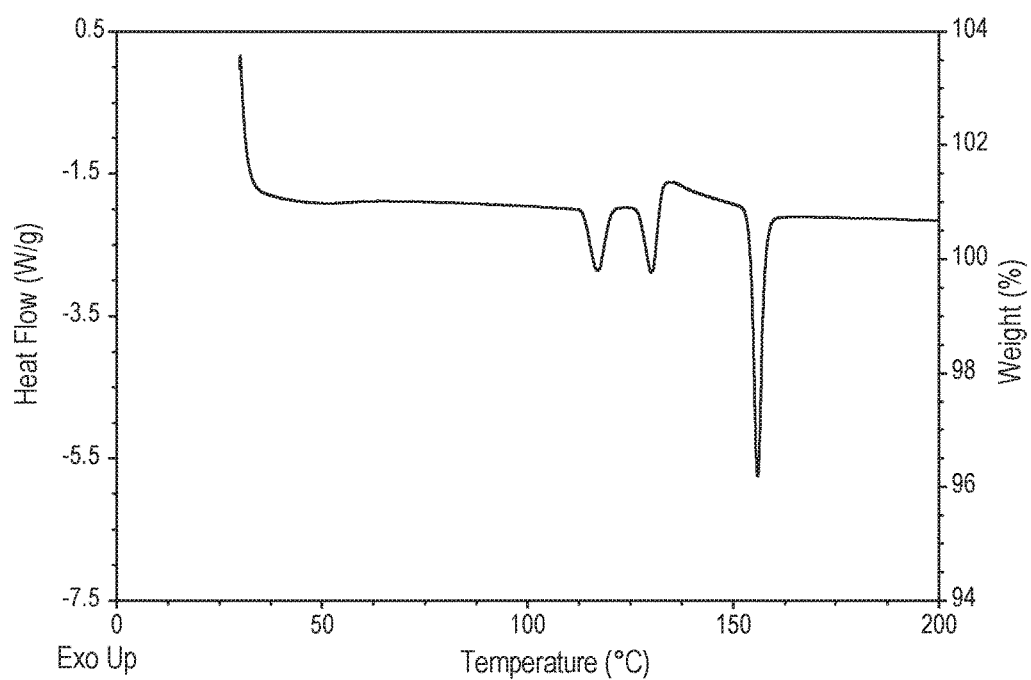
FIG. 4B depicts a DSC thermograph of the free base acetone solvate form of Compound M when the sample is heated from 25° C. at a rate of 10° C./min.

The free base acetone solvate form of Compound M can be characterized by its DSC thermograph, obtained as set forth in the Methods section. In embodiments, the free base acetone solvate form of Compound M can be characterized by a DSC thermograph, obtained at a heating rate of 10° C./min, having and endothermic event with an onset at about 114° C. with a peak at about 117° C., as depicted in FIG. 4B. In embodiments, the free base acetone solvate form of Compound M can be characterized by a DSC thermograph substantially as depicted in FIG. 4B.

The free base acetone solvate form of Compound M be formed in a variety of ways. In one type of embodiment, the free base acetone solvate form of Compound M can be formed by preparing a slurry of the free base monohydrate form of Compound M in acetone, and isolating the resulting solid.

DMSO Hemisolvate Form of Compound M

In another aspect, the disclosure provides a dimethylsulfoxide (DMSO) hemisolvate form of Compound M. The DMSO hemisolvate form of Compound M has a solubility of about 164 mg/mL at a temperature in the range of about 20 to about 25° C. The DMSO hemisolvate form of Compound M can be characterized by one or more of the parameters described below.

In embodiments, the DMSO hemisolvate form of Compound M can include about a 1:2 molar ratio of DMSO to Compound M.

Figure 5A:
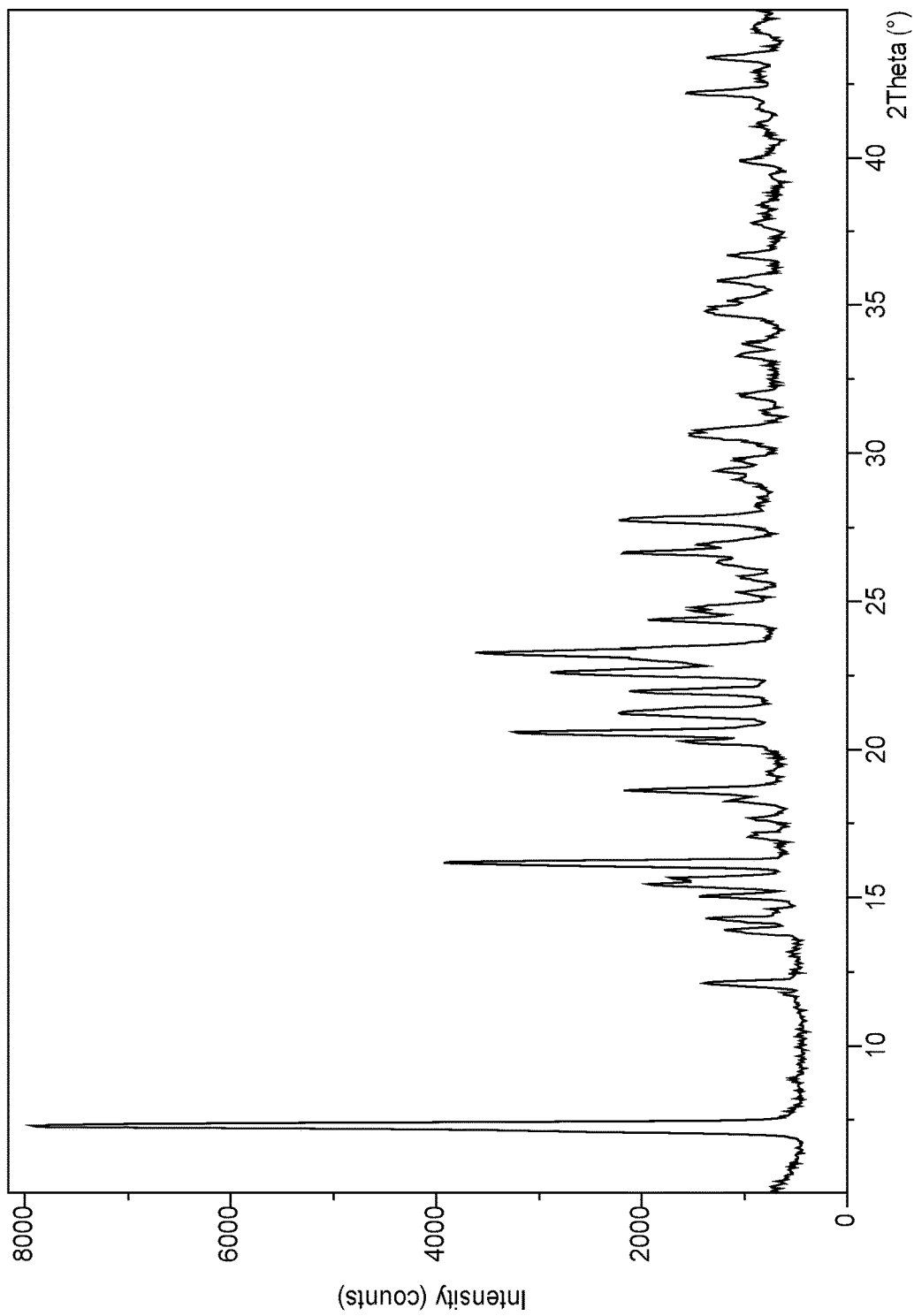
FIG. 5A depicts an XRPD pattern of the free DMSO hemisolvate form of Compound M.

The free base DMSO hemisolvate form of Compound M can be characterized by an X-ray powder diffraction pattern, obtained as set forth in the Methods section, having peaks at about 7.3, 13.9, 14.3, 16.2, and 27.8±0.2° 2θ using Cu Kα radiation. The free base DMSO hemisolvate form of Compound M optionally can be further characterized by an X-ray powder diffraction pattern having additional peaks at about 12.1, 15.0, 15.4, 15.6, 18.6, 20.6, 21.2, 22.0, 22.6, and 23.2±0.2° 2θ using Cu Kα radiation. In some embodiments, the free base DMSO hemisolvate form of Compound M can be characterized by an X-ray powder diffraction pattern substantially as depicted in FIG. 5A.

Figure 5B:
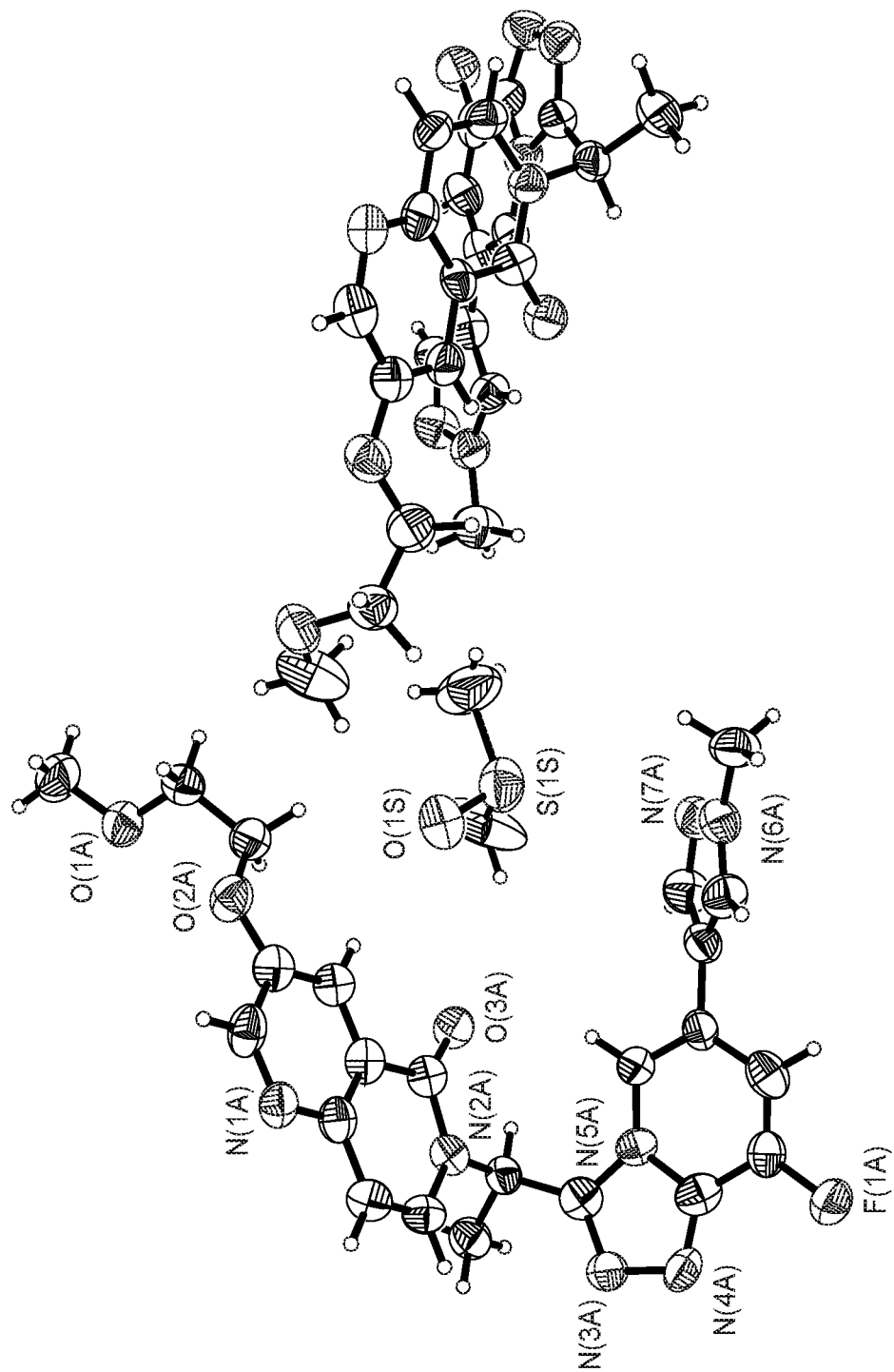
FIG. 5B depicts a single crystal XRD structure of the free base DMSO hemisolvate form of Compound M.

In one embodiment, the free base DMSO hemisolvate form of Compound M can be characterized by a single crystal XRD pattern, obtained as set forth in the Methods section, wherein the free base DMSO hemisolvate form comprises a monoclinic space group of C2 and unit cell parameters of about a=25.6737(16) Å, b=8.2040(5) Å, c=24.1194(12) Å, and β=107.436(4)°. The free base DMSO hemisolvate form of Compound M optionally can be further characterized by the XRD parameters in the table, below, and as represented in FIG. 5B.

| | |
|---|---|
| Wavelength | 1.54178 Å |
| Crystal system | Monoclinic |
| Space group | C2 |
| Unit cell dimensions | a = 25.6737(16) Å |
| | α = γ = 90° |
| | b = 8.2040(5) Å |
| | β = 107.436(4)° |
| | c = 24.1194(12) Å |
| Volume | 4846.8(5) Å$^3$ |
| Z | 8 |
| Density (calculated) | 1.377 Mg/m$^3$ |
| Flack parameter | 0.02(6) |

Figure 5C:
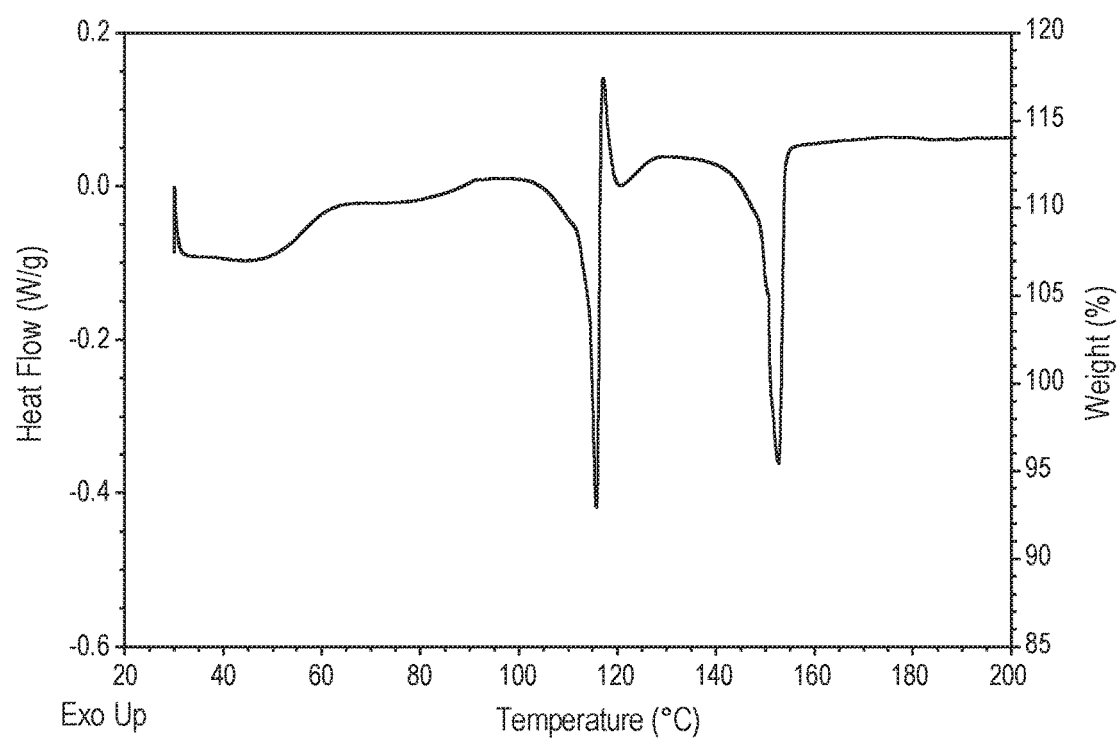
FIG. 5C depicts a DSC thermograph of the free base DMSO hemisolvate form of Compound M.

The free base DMSO hemisolvate form of Compound M can be characterized by a DSC thermograph, as set forth in the Methods section. In embodiments, the free base DMSO hemisolvate form of Compound M can be characterized by a DSC thermograph, obtained at a heating rate of 10° C./min, and having a first melting event at about 114° C., and/or a recrystallization exotherm at about 117° C., and/or a melt onset temperature at about 150° C., as depicted in FIG. 5C. In embodiments, the free base DMSO hemisolvate form of Compound M can be characterized by a DSC thermograph substantially as depicted in FIG. 5C.

The free base DMSO hemisolvate form of Compound M can be formed in a variety of ways. In one type of embodiment, the free base DMSO hemisolvate form of Compound M can be formed by preparing a slurry of the free base monohydrate form of Compound M in DMSO, and isolating the resulting solid.

Amorphous Form of Compound M

In still another aspect, the disclosure provides an amorphous form of Compound M. The amorphous form of Compound M can be characterized by one or more of the parameters described below.

Figure 6A:
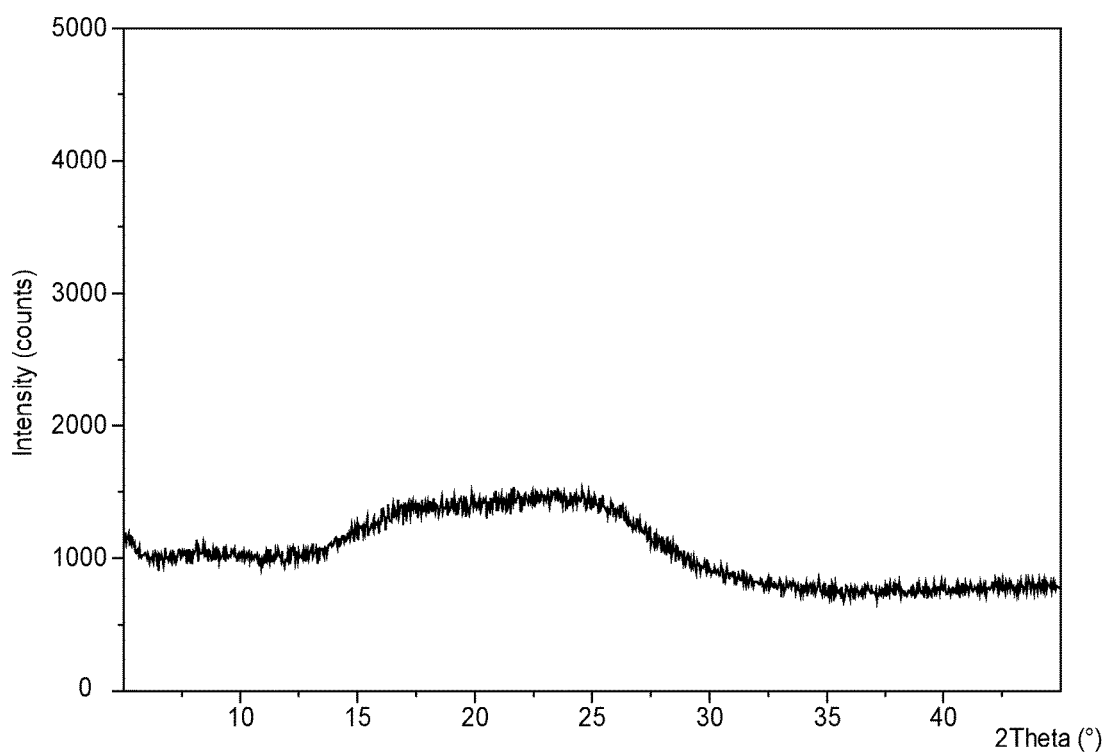
FIG. 6A depicts an XRPD pattern of the free base amorphous form of Compound M.

In embodiments, the free base amorphous form of Compound M can be characterized by an XRPD pattern, obtained as set forth in the Methods section, having no defined peaks. For example, the free base amorphous form of Compound M can be characterized by an XRPD pattern substantially as depicted in FIG. 6A.

Figure 6B:
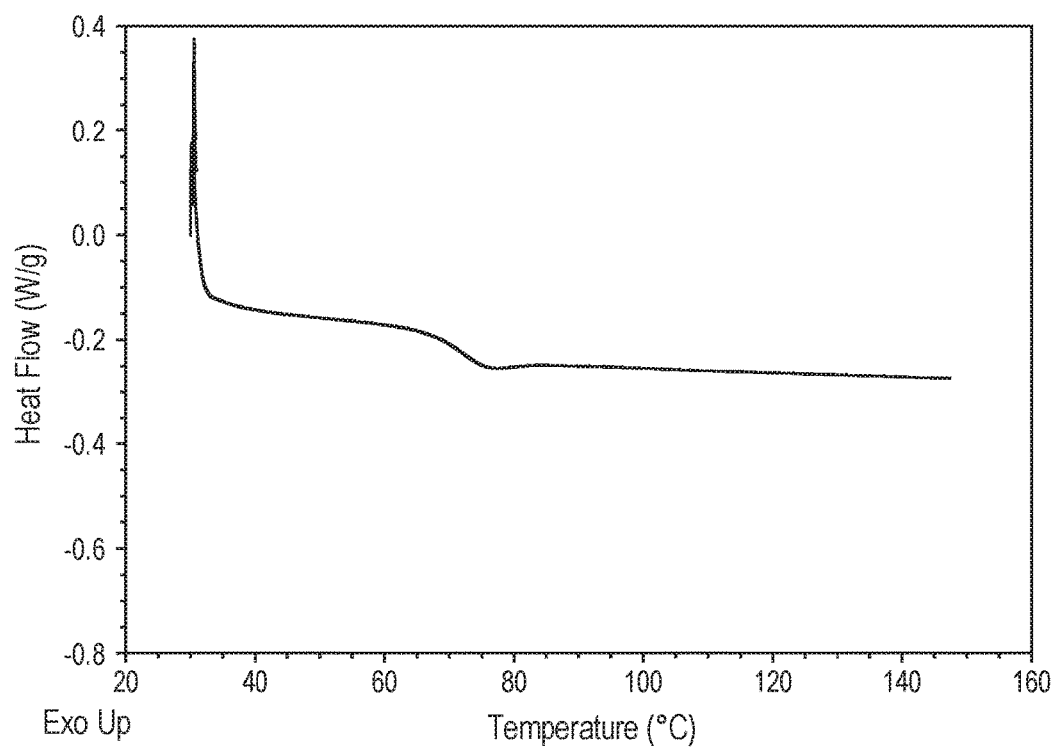
FIG. 6B depicts a DSC thermograph of the free base amorphous form of Compound M.

In embodiments, the free base amorphous form of Compound M can be characterized by a DSC trace, obtained as set forth in the Methods section, showing a glass transition (Tg) at about 72° C. For example, the free base amorphous form of Compound M can be characterized by a DSC thermograph substantially as depicted in FIG. 6B.

The free base amorphous form of Compound M can be formed in a variety of ways. In one type of embodiment, the free base amorphous form of Compound M can be formed by evaporating a crude reaction mixture of Compound M onto a substrate (e.g., silica gel), purifying the crude reaction mixture via flash chromatography, collecting the resulting solution, and evaporating the solvent.

Co-Crystal Forms of Compound M

In another aspect, the disclosure provides a co-crystal form of Compound M having a co-crystal forming compound ("coformer") selected from the group consisting of phosphoric acid, maleic acid, succinic acid, sorbic acid, glutaric acid, and urea.

Phosphoric Acid Co-Crystal of Compound M

Figure 7A:
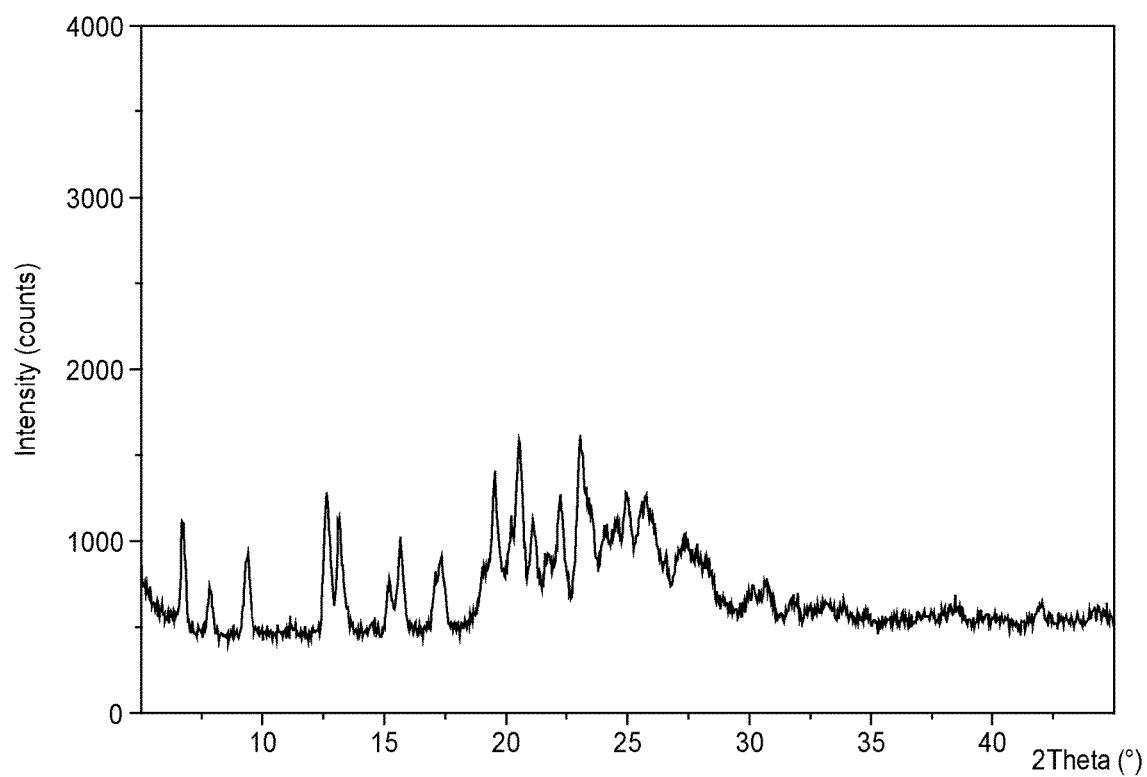
FIG. 7A depicts an XRPD pattern of a phosphoric acid co-crystal of Compound M.

In one type of embodiment, the coformer is phosphoric acid. In these embodiments, the phosphoric acid co-crystal of Compound M can include about a 1:1 molar ratio of phosphoric acid to Compound M. The phosphoric acid co-crystal form of Compound M can be characterized by an XRPD pattern, obtained as set forth in the Methods section, having peaks at about 9.4, 12.7, 17.3, 21.1, and 23.1±0.2° 2θ using Cu Kα radiation. The phosphoric acid co-crystal form of Compound M optionally can be further characterized by an X-ray powder diffraction pattern having additional peaks at about 6.7, 7.8, 13.2, 15.7, 19.5, 20.5, and 24.8±0.2° 2θ using Cu Kα radiation. In embodiments, the phosphoric acid co-crystal form of Compound M can be characterized by an X-ray powder diffraction pattern substantially as depicted in FIG. 7A.

Figure 7B:
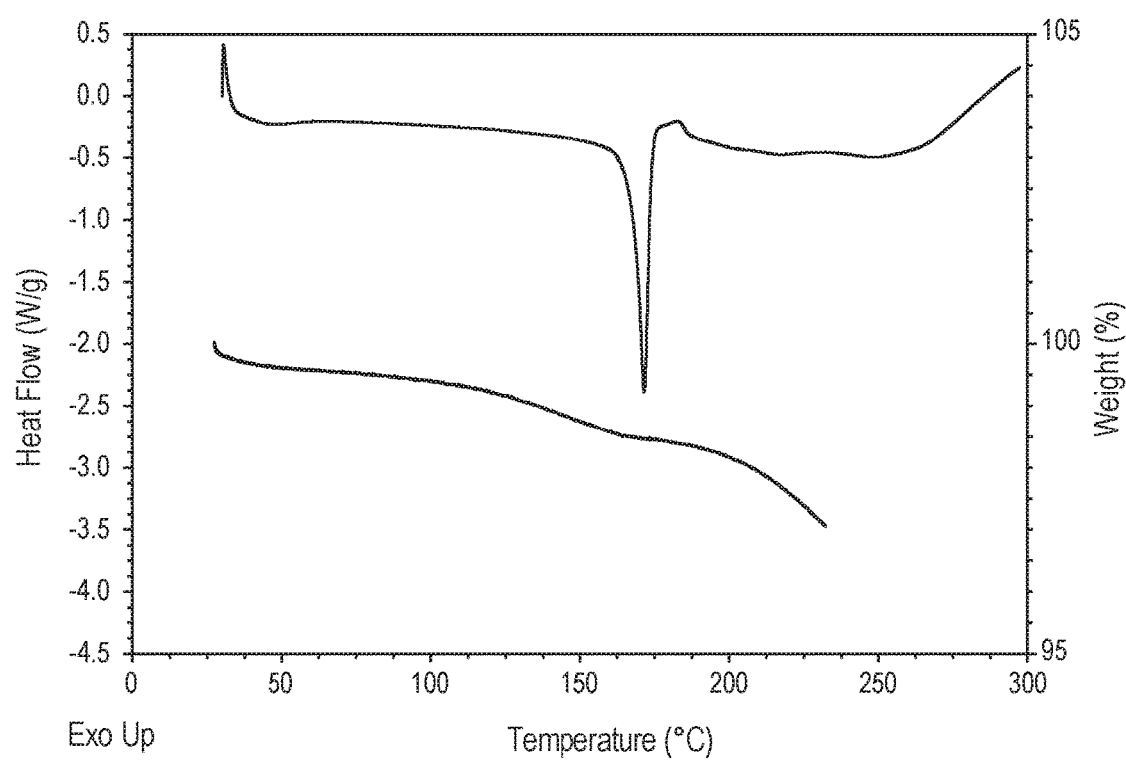
FIG. 7B depicts a DSC thermograph (top trace) and a TGA trace (bottom trace) of the phosphoric acid co-crystal of Compound M when the sample is heated from 25° C. at a rate of 10° C./min.

The phosphoric acid co-crystal of Compound M can be characterized by a DSC thermograph, as set forth in the Methods section. In embodiments, the phosphoric acid co-crystal of Compound M can be characterized by a DSC thermograph having a melt endotherm with an onset in a range of about 166° C. to about 169° C. when the phosphoric acid co-crystal is heated in an open aluminum pan. For example, when embodiments of the phosphoric acid co-crystal of Compound M are heated from about 25° C. at a rate of about 10° C./min, the phosphoric acid co-crystal of Compound M can be characterized by a DSC thermograph having a melt endotherm with an onset of about 168° C., as depicted in FIG. 7B (top trace). In embodiments, the phosphoric acid co-crystal of Compound M can be characterized by a DSC thermograph substantially as depicted in FIG. 7B (top trace).

In embodiments, the phosphoric acid co-crystal of Compound M can be characterized by TGA, as set forth in the Methods section. Thus, in embodiments, the phosphoric acid co-crystal of Compound M can be characterized by a TGA trace substantially as depicted in FIG. 7B (bottom trace).

Maleic Acid Co-Crystal of Compound M

Figure 8A:
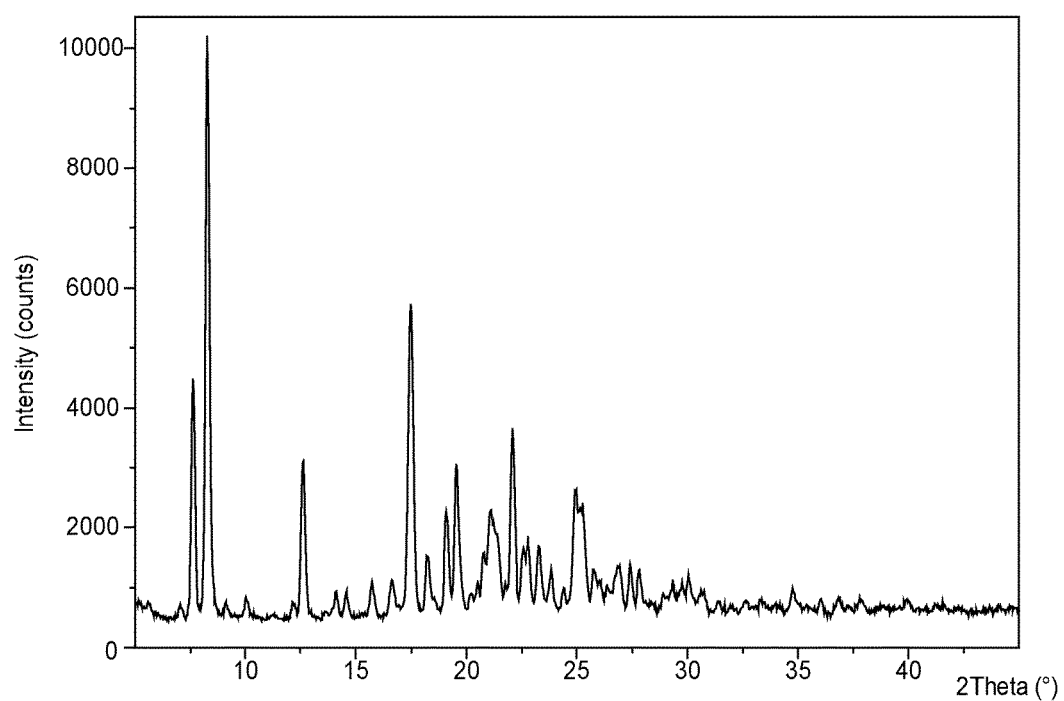
FIG. 8A depicts an XRPD pattern of a maleic acid co-crystal of Compound M.

In another type of embodiment, the coformer is maleic acid. In these embodiments, the maleic acid co-crystal of Compound M can include about a 1:1 molar ratio of maleic acid to Compound M. The maleic acid co-crystal form of Compound M can be characterized by an XRPD pattern, obtained as set forth in the Methods section, having peaks at about 10.0, 12.6, 17.5, 21.1, and 23.3±0.2° 2θ using Cu Kα radiation. The maleic acid co-crystal form of Compound M optionally can be further characterized by an X-ray powder diffraction pattern having additional peaks at about 7.7, 8.3, 15.7, 19.5, 20.5, and 22.3±0.2° 2θ using Cu Kα radiation. In embodiments, the maleic acid co-crystal form of Compound M can be characterized by an X-ray powder diffraction pattern substantially as depicted in FIG. 8A.

Figure 8B:
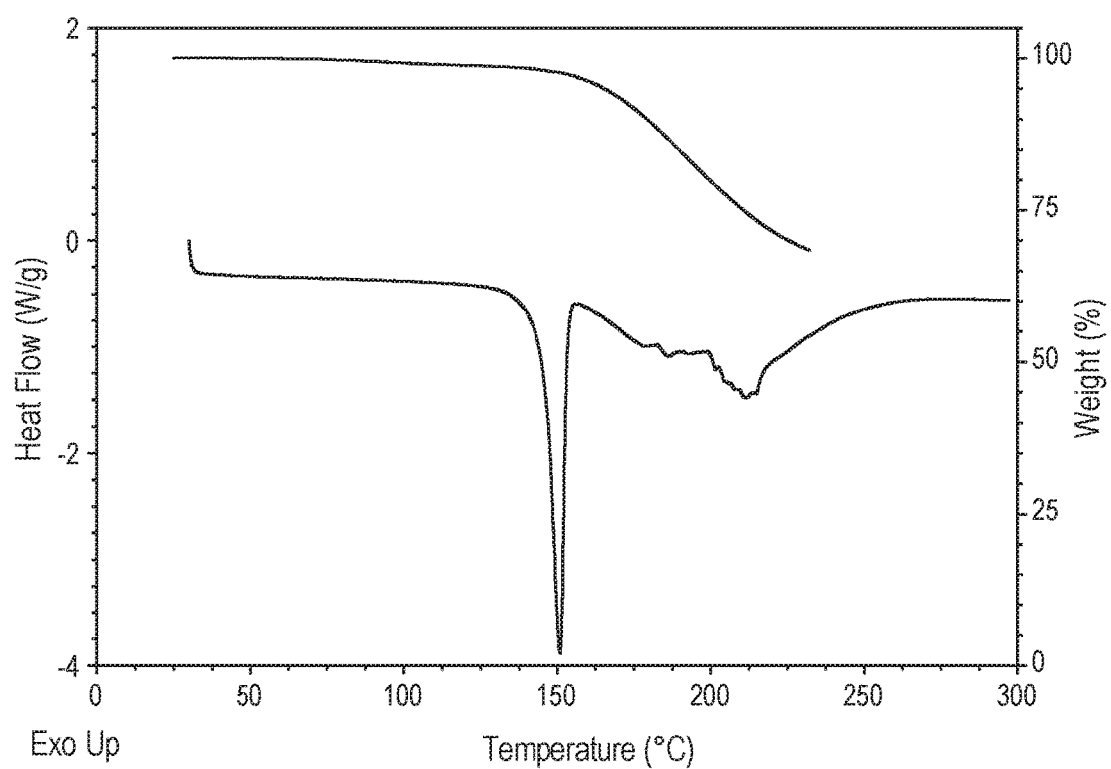
FIG. 8B depicts a DSC thermograph (bottom trace) and a TGA trace (top trace) of the maleic acid co-crystal of Compound M when the sample is heated from 25° C. at a rate of 10° C./min.

The maleic acid co-crystal of Compound M can be characterized by a DSC thermograph, as set forth in the Methods section. In embodiments, the maleic acid co-crystal of Compound M can be characterized by a DSC thermograph having a melt endotherm with an onset in a range of about 151° C. to about 154° C. when the maleic acid co-crystal of Compound M is heated in an open aluminum pan. For example, when embodiments of the maleic acid co-crystal of Compound M are heated from about 25° C. at a rate of about 10° C./min, the maleic acid co-crystal of Compound M can be characterized by a DSC thermograph having a melt endotherm with an onset of about 152° C., as depicted in FIG. 8B (bottom trace). In embodiments, the maleic acid co-crystal of Compound M can be characterized by a DSC thermograph substantially as depicted in FIG. 8B (bottom trace).

In embodiments, the maleic acid co-crystal of Compound M can be characterized by TGA. TGA thermographs were obtained as set forth in the Methods section. Thus, in embodiments, the maleic acid co-crystal of Compound M can be characterized by a TGA trace substantially as depicted in FIG. 8B (top trace).

In embodiments, the maleic acid co-crystal of Compound M can be characterized by $^1$H NMR, as set forth in the Methods section. For example, the maleic acid co-crystal of Compound M can be characterized by an NMR spectrum having the following peaks: $^1$H NMR (400 MHz, DMSO-$d_6$): δ 8.69 (d, J=3.0 Hz, 1H), 8.48 (d, J=1.1 Hz, 1H), 8.18 (s, 1H), 8.02 (d, J=3.0 Hz, 1H), 7.84 (d, J=0.8 Hz, 1H), 7.67 (dd, J=12.1 Hz, J=1.2 Hz, 1H), 7.61 (d, J=7.8 Hz, 1H), 6.94 (q, J=7.1 Hz, 1H), 6.76 (d, J=7.7 Hz, 1H), 6.24 (s, 2H), 4.30 (m, 2H), 3.89 (s, 3H), 3.71 (m, 2H), 2.43 (s, 8H), 1.99 (d, J=7.1 Hz, 3H).

Succinic Acid Co-Crystal of Compound M

Figure 9A:
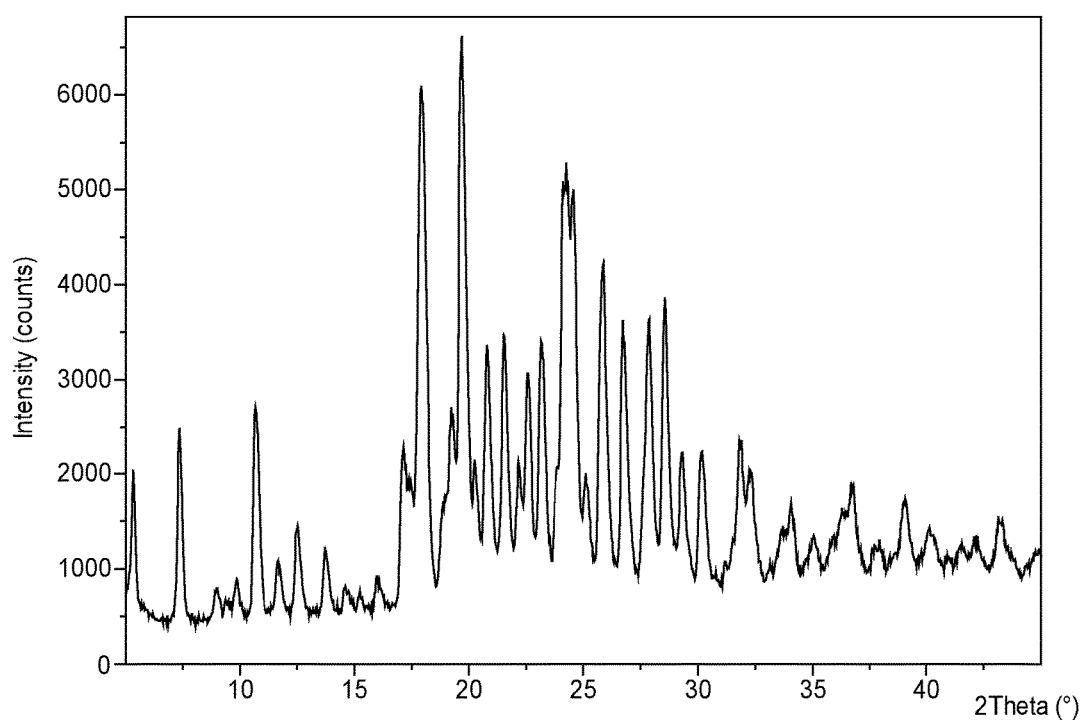
FIG. 9A depicts an XRPD pattern of a succinic acid co-crystal of Compound M.

In yet another type of embodiment, the coformer is succinic acid. In these embodiments, the succinic acid co-crystal of Compound M can include about a 2:1 molar ratio of succinic acid to Compound M. The succinic acid co-crystal form of Compound M can be characterized by an XRPD pattern, obtained as set forth in the Methods section, having peaks at about 5.3, 10.7, 12.5, 13.7, and 26.8±0.2° 2θ using Cu Kα radiation. The succinic acid co-crystal form of Compound M optionally can be further characterized by an X-ray powder diffraction pattern having additional peaks at about 7.4, 17.9, 19.7, 20.8, 21.6, 23.2, 25.8, 27.9, and 28.6±0.2° 2θ using Cu Kα radiation. In embodiments, the succinic acid co-crystal form of Compound M can be characterized by an X-ray powder diffraction pattern substantially as depicted in FIG. 9A.

Figure 9B:
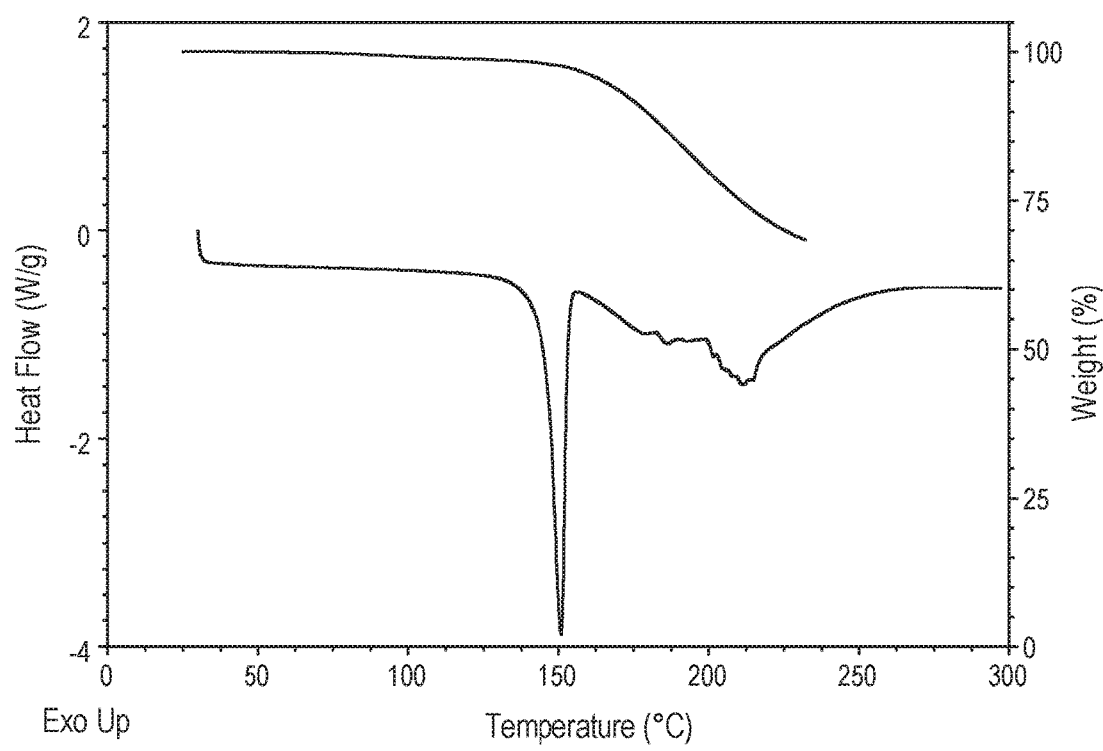
FIG. 9B depicts a DSC thermograph (bottom trace) and a TGA trace (top trace) of the succinic acid co-crystal of Compound M when the sample is heated from 25° C. at a rate of 10° C./min.

The succinic acid co-crystal of Compound M can be characterized by a DSC thermograph, as set forth in the Methods section. In embodiments, the succinic acid co-crystal of Compound M can be characterized by a DSC thermograph having a melt endotherm with an onset in a range of about 148° C. to about 154° C. when the succinic acid co-crystal is heated in an open aluminum pan. For example, when embodiments of the succinic acid co-crystal of Compound M are heated from about 25° C. at a rate of about 10° C./min, the succinic acid co-crystal of Compound M can be characterized by a DSC thermograph having a melt endotherm with an onset of about 151° C., as depicted in FIG. 9B (bottom trace). In embodiments, the succinic acid co-crystal of Compound M can be characterized by a DSC thermograph substantially as depicted in FIG. 9B (bottom trace).

In embodiments, the succinic acid co-crystal of Compound M can be characterized by TGA. TGA thermographs were obtained as set forth in the Methods section. Thus, in embodiments, the succinic acid co-crystal of Compound M can be characterized by a TGA trace substantially as depicted in FIG. 9B (top trace).

In embodiments, the succinic acid co-crystal of Compound M can be characterized by $^1$H NMR, as set forth in the Methods section. For example, the succinic acid co-crystal of Compound M can be characterized by an NMR spectrum having the following peaks: $^1$H NMR (400 MHz, DMSO-$d_6$): δ 12.12 (bs, ~3-4H), 8.70 (d, J=3.0 Hz, 1H), 8.49 (d, J=1.2 Hz, 1H), 8.18 (s, 1H), 8.03 (d, J=2.6 Hz, 1H), 7.85 (d, J=0.8 Hz, 1H), 7.68 (dd, J=12.1 Hz, J=1.2 Hz, 1H), 7.62 (d, J=7.8 Hz, 1H), 6.95 (q, J=7.2 Hz, 1H), 6.77 (d, J=8.1 Hz, 1H), 4.31 (m, 2H), 3.89 (s, 3H), 3.72 (m, 2H), 2.43 (s, 8H), 2.00 (d, J=7.1 Hz, 3H).

Sorbic Acid Co-Crystal of Compound M

Figure 10A:
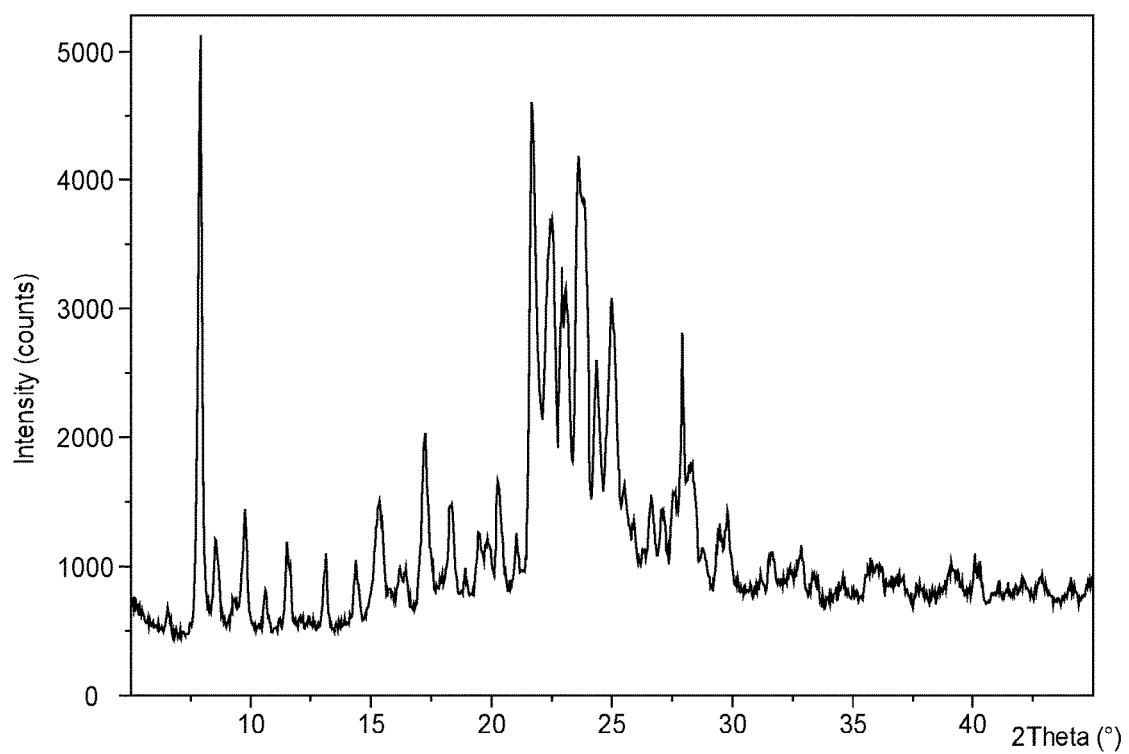
FIG. 10A depicts an XRPD pattern of a sorbic acid co-crystal of Compound M.

In still another type of embodiment, the coformer is sorbic acid. In these embodiments, the sorbic acid co-crystal of Compound M can include about a 2:1 molar ratio of sorbic acid to Compound M. The sorbic acid co-crystal form of Compound M can be characterized by an XRPD pattern, obtained as set forth in the Methods section, having peaks at about 7.9, 8.5, 9.7, 17.2, and 22.4±0.2° 2θ using Cu Kα radiation. The sorbic acid co-crystal form of Compound M optionally can be further characterized by an X-ray powder diffraction pattern having additional peaks at about 11.5, 13.1, 15.3, 18.3, 20.3, 21.7, 23.6, 25.0, and 27.9±0.2° 2θ using Cu Kα radiation. In embodiments, the sorbic acid co-crystal form of Compound M can be characterized by an X-ray powder diffraction pattern substantially as depicted in FIG. 10A.

Figure 10B:
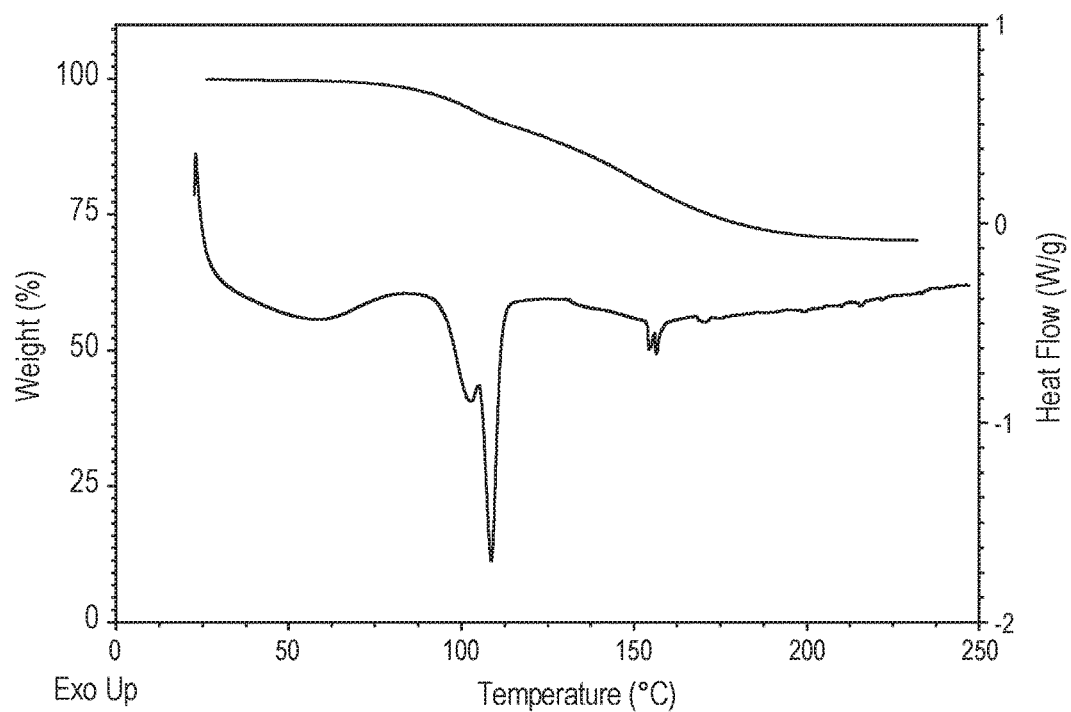
FIG. 10B depicts a DSC thermograph (bottom trace) and a TGA trace (top trace) of the sorbic acid co-crystal of Compound M when the sample is heated from 25° C. at a rate of 10° C./min.

The sorbic acid co-crystal of Compound M can be characterized by a DSC thermograph, as set forth in the Methods section. In embodiments, the sorbic acid co-crystal of Compound M can be characterized by a DSC thermograph having an endotherm with an onset in a range of about 102° C. to about 106° C. when the sorbic acid co-crystal is heated in an open aluminum pan. For example, in embodiments wherein the sorbic acid co-crystal of Compound M is heated from about 25° C. at a rate of about 10° C./min, the sorbic acid co-crystal of Compound M can be characterized by a DSC thermograph having an endotherm with an onset of about 104° C., as shown in FIG. 10B (bottom trace). In embodiments, the sorbic acid co-crystal of Compound M can be characterized by a DSC thermograph substantially as depicted in FIG. 10B (bottom trace).

In embodiments, the sorbic acid co-crystal of Compound M can be characterized by TGA. TGA thermographs were obtained as set forth in the Methods section. Thus, in embodiments, the sorbic acid co-crystal of Compound M can be characterized by a TGA trace substantially as depicted in FIG. 10B (top trace).

In embodiments, the sorbic acid co-crystal of Compound M can be characterized by $^1$H NMR, as set forth in the Methods section. For example, the sorbic acid co-crystal of Compound M can be characterized by an NMR spectrum having the following peaks: $^1$H NMR (400 MHz, DMSO-$d_6$): δ 12.09 (bs, 2H), 8.69 (d, J=3.0 Hz, 1H), 8.48 (d, J=1.1 Hz, 1H), 8.17 (s, 1H), 8.02 (d, J=3.0 Hz, 1H), 7.84 (d, J=0.9 Hz, 1H), 7.67 (dd, J=12.1 Hz, J=1.2 Hz, 1H), 7.61 (d, J=7.8 Hz, 1H), 7.14 (dd, J=15.1 Hz, J=10.1 Hz, 2H), 6.94 (q, J=7.0, 1H), 6.76 (d, J=7.8 Hz, 1H), 6.24 (m, 4H), 5.77 (m, 2H) 4.30 (m, 2H), 3.89 (s, 3H), 3.71 (m, 2H), 1.99 (d, J=7.0 Hz, 3H), 1.81 (m, 6H).

Glutaric Acid Co-Crystal of Compound M

Figure 11A:
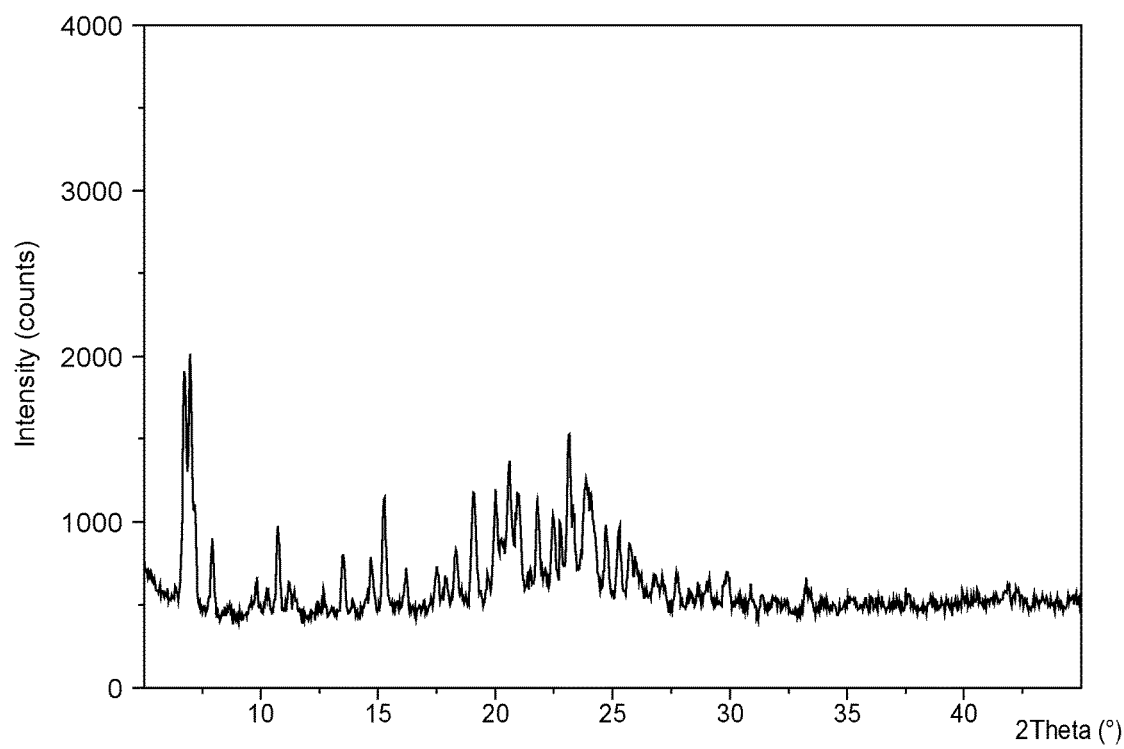
FIG. 11A depicts an XRPD pattern of a glutaric acid co-crystal of Compound M.

In another type of embodiment, the coformer is glutaric acid. In these embodiments, the glutaric acid co-crystal of Compound M can include about a 2:1 molar ratio of glutaric acid to Compound M. The glutaric acid co-crystal form of Compound M can be characterized by an XRPD pattern, obtained as set forth in the Methods section, having peaks at about 6.7, 7.0, 10.7, 15.3, and 21.0±0.2° 2θ using Cu Kα radiation. The glutaric acid co-crystal form of Compound M optionally can be further characterized by an X-ray powder diffraction pattern having additional peaks at about 7.9, 13.5, 14.7, 16.2, 18.3, 19.1, 20.6, 23.2, 24.7, and 25.3±0.2° 2θ using Cu Kα radiation. In embodiments, the glutaric acid co-crystal form of Compound M can be characterized by an X-ray powder diffraction pattern substantially as depicted in FIG. 11A.

Figure 11B:
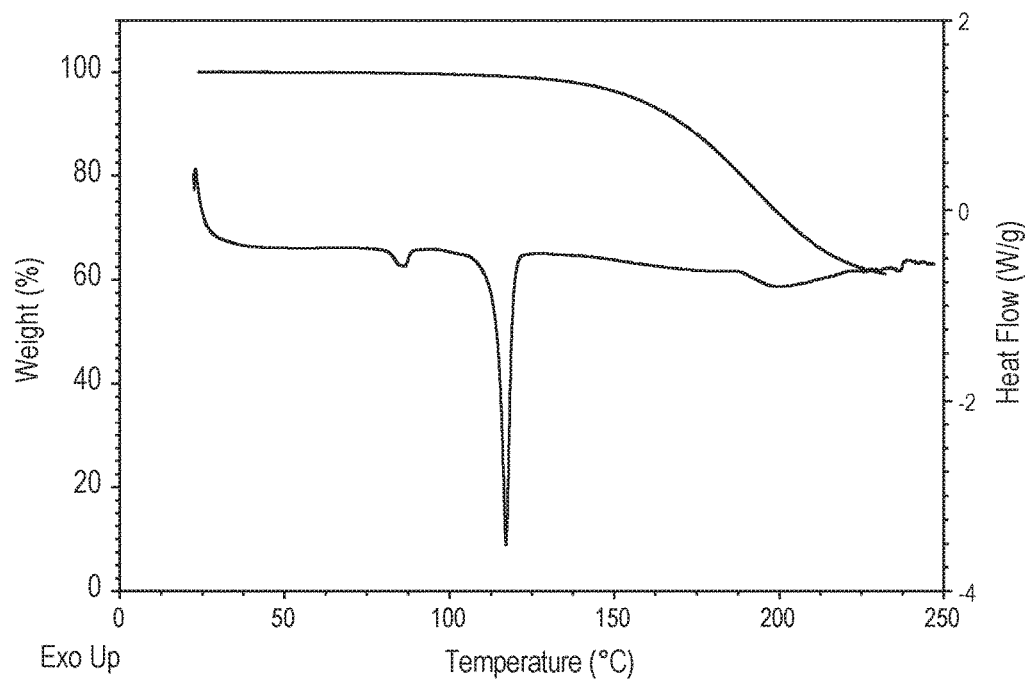
FIG. 11B depicts a DSC thermograph (bottom trace) and a TGA trace (top trace) of the glutaric acid co-crystal of Compound M when the sample is heated from 25° C. at a rate of 10° C./min.

The glutaric acid co-crystal of Compound M can be characterized by a DSC thermograph, as set forth in the Methods section. In embodiments, the glutaric acid co-crystal of Compound M can be characterized by a DSC thermograph having an endotherm with an onset in a range of about 75° C. to about 82° C. and/or in a range of about 113° C. to about 115° C. when the glutaric acid co-crystal is heated in an open aluminum pan. For example, in embodiments wherein the glutaric acid co-crystal of Compound M is heated from about 25° C. at a rate of about 10° C./min, the glutaric acid co-crystal of Compound M can be characterized by a DSC thermograph having endotherms with onsets of about 82° C. and about 114° C., as shown in FIG. 11B (bottom trace). In embodiments, the sorbic acid co-crystal of Compound M can be characterized by a DSC thermograph substantially as depicted in FIG. 11B (bottom trace).

In embodiments, the glutaric acid co-crystal of Compound M can be characterized by TGA. TGA thermographs were obtained as set forth in the Methods section. Thus, in embodiments, the glutaric acid co-crystal of Compound M can be characterized by a TGA trace substantially as depicted in FIG. 11B (top trace).

In embodiments, the glutaric acid co-crystal of Compound M can be characterized by $^1$H NMR, as set forth in the Methods section. For example, the glutaric acid co-crystal of Compound M can be characterized by an NMR spectrum having the following peaks: $^1$H NMR (400 MHz, DMSO-$d_6$): δ 12.06 (bs, 4H), 8.70 (d, J=3.0 Hz, 1H), 8.49 (d, J=1.1 Hz, 1H), 8.18 (s, 1H), 8.03 (d, J=2.4 Hz, 1H), 7.85 (d, J=0.8 Hz, 1H), 7.68 (dd, J=12.1 Hz, J=1.2 Hz, 1H), 7.62 (d, J=7.8 Hz, 1H), 6.95 (q, J=7.0 Hz, 1H), 6.77 (d, J=7.8 Hz, 1H), 4.31 (m, 2H), 3.90 (s, 3H), 3.72 (m, 2H), 2.25 (t, J=7.4 Hz, ~8-9H), 2.00 (d, J=7.0 Hz, 3H), 1.71 (quin, J=7.3 Hz, 4H).

Urea Co-Crystal of Compound M

Figure 12A:
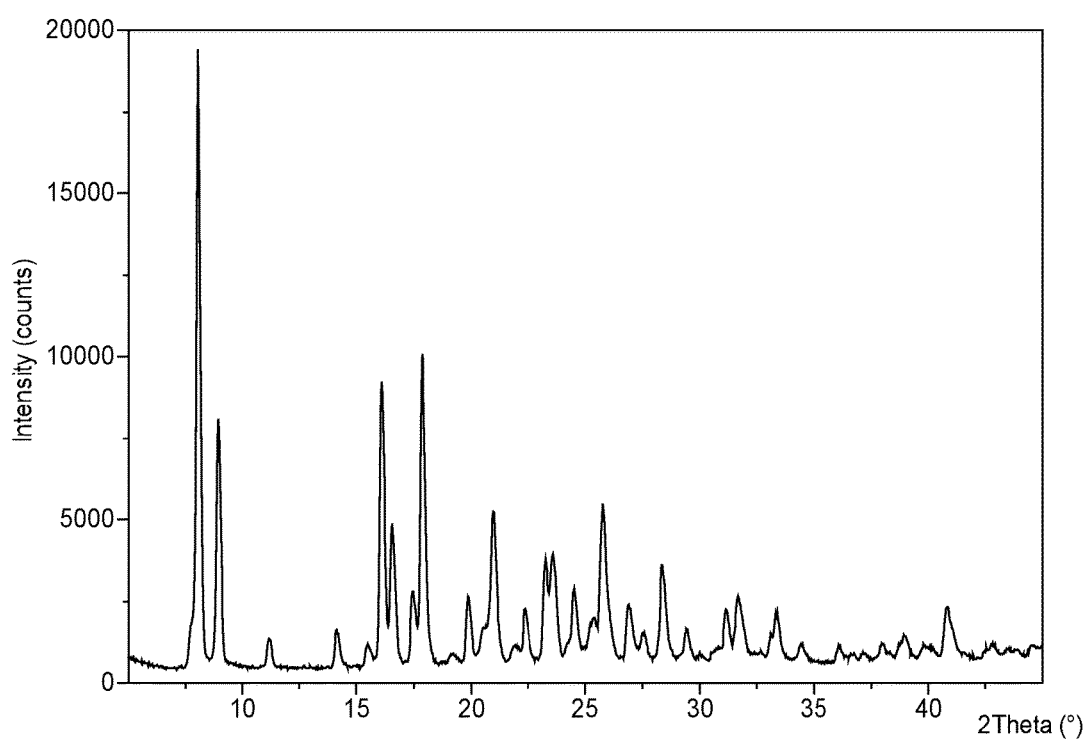
FIG. 12A depicts an XRPD pattern of a urea co-crystal of Compound M.

In yet another type of embodiment, the coformer is urea, wherein the urea co-crystal of Compound M can include about a 1:1 molar ratio of urea to Compound M. The urea co-crystal form of Compound M can be characterized by an XRPD pattern, obtained as set forth in the Methods section, having peaks at about 8.1, 8.9, 16.1, 21.0, and 28.4±0.2° 2θ using Cu Kα radiation. The urea co-crystal form of Compound M optionally can be further characterized by an X-ray powder diffraction pattern having additional peaks at about 11.2, 14.2, 16.6, 17.5, 17.9, 19.9, 22.4, 24.5, and 25.8±0.2° 2θ using Cu Kα radiation. In embodiments, the urea co-crystal form of Compound M can be characterized by an X-ray powder diffraction pattern substantially as depicted in FIG. 12A.

Figure 12B:
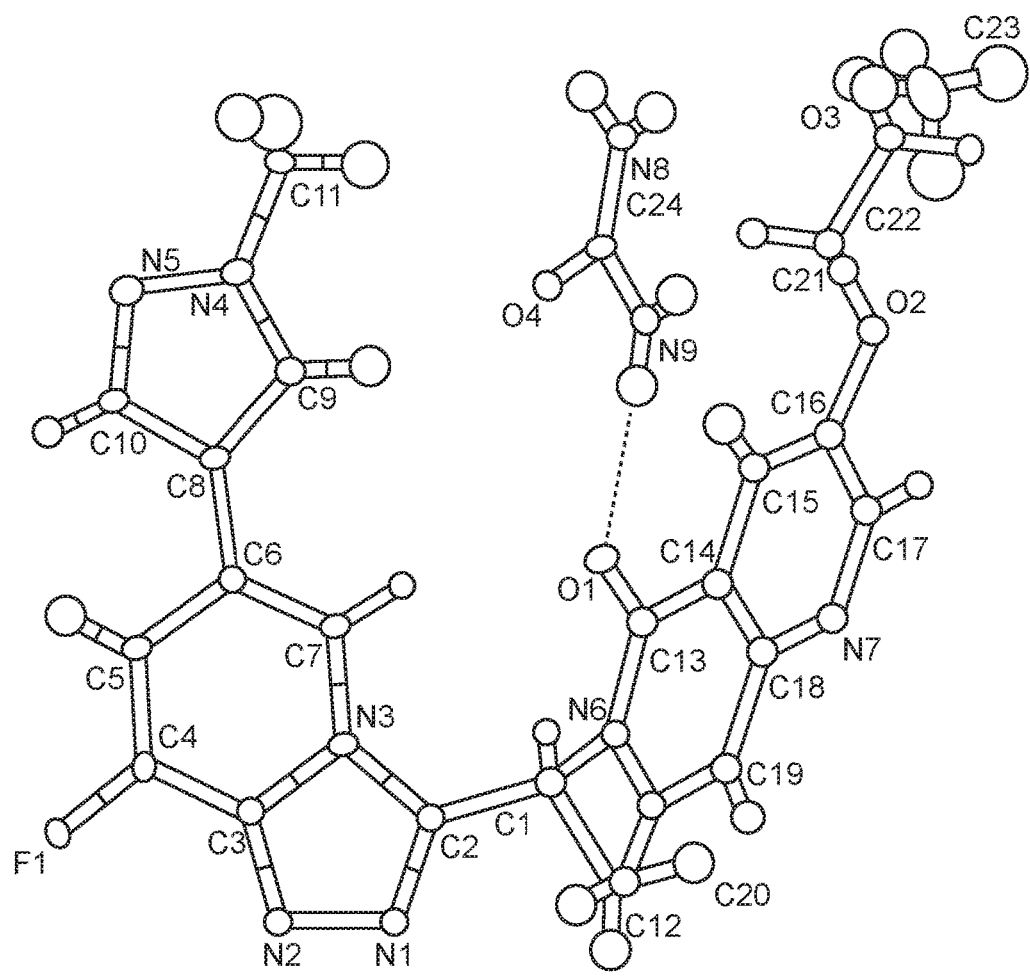
FIG. 12B depicts a single crystal XRD structure of a urea co-crystal of Compound M.

In one embodiment, the urea co-crystal form of Compound M can be characterized by a single crystal XRD structure, obtained as set forth in the Methods section, wherein the urea co-crystal form of Compound M comprises a monoclinic space group of $P2_1$ and unit cell parameters of about a=4.7057(2) Å, b=22.7810(11) Å, c=10.9512(6) Å, and β=91.361(2)°. The urea co-crystal form of Compound M optionally can be further characterized by the XRD parameters in the table below, and as represented in FIG. 12B.

| Crystal system | Monoclinic |
|---|---|
| Space group | $P2_1$ |
| Wavelength | 0.71073 Å |
| Unit cell dimensions | a = 4.7057(2) Å; α = 90°. |
| | b = 22.7810(11) Å; β = 91.361(2)° |
| | c = 10.9512(6) Å; γ = 90° |
| Volume | 1173.64(10) Å$^3$ |
| Z | 2 |
| Density (calculated) | 1.481 mg/m$^3$ |

Figure 12C:
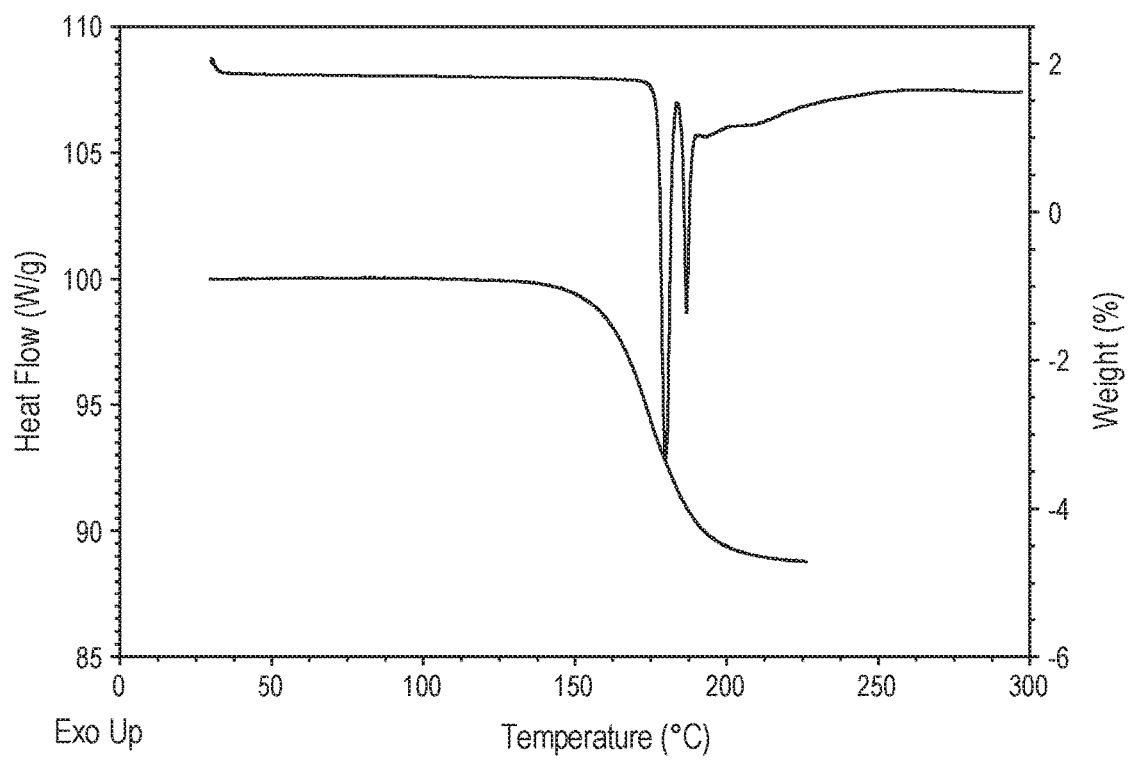
FIG. 12C depicts a DSC thermograph (top trace) and a TGA trace (bottom trace) of the urea co-crystal of Compound M when the sample is heated from 25° C. at a rate of 10° C./min.

The urea co-crystal of Compound M can be characterized by a DSC thermograph, as set forth in the Methods section. In embodiments, the urea co-crystal of Compound M can be characterized by a DSC thermograph having endotherms with onsets in a range of about 177° C. to about 179° C. when the urea co-crystal is heated in an open aluminum pan. For example, in embodiments wherein the urea co-crystal of Compound M is heated from about 25° C. at a rate of about 10° C./min, the urea co-crystal of Compound M can be characterized by a DSC thermograph having an endotherm with an onset of about 178° C., as shown in FIG. 12C (top trace). In embodiments, the urea co-crystal of Compound M can be characterized by a DSC thermograph substantially as depicted in FIG. 12C (top trace).

In embodiments, the urea co-crystal of Compound M can be characterized by TGA. TGA thermographs were obtained as set forth in the Methods section. Thus, in embodiments, the urea co-crystal of Compound M can be characterized by a TGA trace substantially as depicted in FIG. 12C (bottom trace).

In embodiments, the urea co-crystal of Compound M can be characterized by $^1$H NMR, as set forth in the Methods section. For example, the urea co-crystal of Compound M can be characterized by an NMR spectrum having the following peaks: $^1$H NMR (400 MHz, DMSO-d$_6$): δ 8.70 (d, J=3.0 Hz, 1H), 8.49 (d, J=1.1 Hz, 1H), 8.19 (s, 1H), 8.03 (d, J=3.0 Hz, 1H), 7.85 (d, J=0.8 Hz, 1H), 7.69 (dd, J=12.1 Hz, J=1.2 Hz, 1H), 7.62 (d, J=7.8 Hz, 1H), 6.95 (q, J=7.2 Hz, 1H), 6.77 (d, J=8.1 Hz, 1H), 5.39 (bs, 4H), 4.31 (tt, J=2.7 Hz, J=1.7 Hz, 2H), 3.90 (s, 3H), 3.72 (tt, J=2.5 Hz, J=1.8 Hz, 2H), 3.32 (s, 12H (6H urea co-crystal, 6H H$_2$O), 2.00 (d, J=7.0 Hz, 3H).

It is contemplated that the polymorphs and co-crystals disclosed herein can be used in the treatment, prevention, or amelioration of cancer, as described in, e.g., U.S. Pat. Nos. 8,212,041, 8,217,177, and U.S. Pat. No. 8,198,448, and U.S. Provisional Patent Application Ser. No. 61/838,856.

Methods

X-ray powder diffraction data were obtained on a PANalytical X'Pert PRO X-ray diffraction system with a Real Time Multiple Strip (RTMS) detector. Samples were scanned in continuous mode from 5-45° (2θ) with a step size of 0.0334° at 45 kV and 40 mA with CuKα radiation (1.54 Å). The incident beam path was equipped with a 0.02 rad soller slit, 15 mm mask, 4° fixed anti-scatter slit and a programmable divergence slit. The diffracted beam was equipped with a 0.02 radian soller slit, programmable anti-scatter slit and a 0.02 mm nickel filter. Samples were prepared on a low background sample holder and placed on a spinning stage with a rotation time of 2 s. For variable-temperature studies, samples were prepared on a flat plate sample holder and placed in a TTK-450 temperature control stage. For variable-humidity studies, RH-200 generator (VTI) was used to control atmosphere in THC humidity sample chamber.

Differential scanning calorimetry (DSC) was performed on a TA Instruments Q100 calorimeter at in an aluminum Tzero pan under dry nitrogen, flowing at 50 mL/min. Thermogravimetric analysis (TGA) was performed on a TA Instruments Q500 analyzer in a platinum pan under dry nitrogen, flowing at 90 mL/min.

Moisture sorption data was collected using a Surface Measurement Systems DVS-Advantage instrument. Equilibrium criteria were set at ±0.002% weight change in 5 minutes with a maximum equilibrium time of 360 minutes.

Single crystal structures were determined as follows. Crystals were mounted on a Nylon loop using a very small amount of paratone oil. Data were collected using a Bruker CCD (charge coupled device) based diffractometer equipped with an Oxford Cryostream low-temperature apparatus operating at 173 K. Data were measured using omega and phi scans of 0.5° per frame for either 30 or 45 s. The total number of images was based on results from the program COSMO where redundancy was expected to be 4.0 and completeness to 100% out to 0.83 Å. Cell parameters were retrieved using APEX II software and refined using SAINT on all observed reflections. Data reduction was performed using the SAINT software which corrects for Lp. Scaling and absorption corrections were applied using SADABS multi-scan technique. The structures were solved by the direct method using the SHELXS-97 program and refined by least squares method on F2, SHELXL-97, which are incorporated in SHELXTL-PC V 6.10.

Throughout the disclosure herein, crystal parameters, such as unit cell dimensions, atomic coordinates, and the like, are provided in standard crystallographic notation, such that the standard uncertainty for a specific value is stated in parentheses. For example, a=12.2708(6) Å indicates a 95% chance that the value of 'a' is 12.2708±0.0006 (i.e., lies between 12.2702 and 12.714 Å).

High performance liquid chromatography (HPLC) analyses were performed on an Agilent 1100 or 1200 series HPLC equipped with a binary pump, diode-array detector, thermostated column compartment, and auto sampler. Separation and elution was achieved using a reverse-phase column and 0.1% triflouroacetic acid/water/acetonitrile mobile phase.

Liquid chromatography mass spectrometry was conducted on an Agilent 1100 LC-MSD Trap SL equipped with an electrospray ionization source. Separation and elution was achieved using a reverse-phase column and 0.1% formic acid/water/acetonitrile mobile phase. Mass spectra data were collected in positive ion mode. Fragmentation data was generated using Auto MS2 mode.

Near-IR spectroscopic analysis was performed using a FOSS NIRSystems near-IR spectrometer that consisted of XDS monochromator and either XDS Rapid Liquid Analyzer or XDS Rapid Content Analyzer, depending on the sample being analyzed. Solid or slurry samples were analyzed directly in sample vials, using empty vials as blanks.

$^1$H NMR was performed on a Bruker BioSpin 400 MHz instrument. Solid samples were dissolved in DMSO-d6 and transferred to NMR tubes for analysis.

EXAMPLES

The following examples are provided for illustration and are not intended to limit the scope of the invention Example 1: Aqueous Solubility of the Free Base Monohydrate Form of Compound M The equilibrium solubility of the free base monohydrate form of Compound M in water was measured in several experiments a temperature in the range of about 20 to 25° C., as shown in the table, below. The aqueous solubility was found to be 0.26 mg/mL and no changes in crystal form were observed based on XRPD analysis of the isolated solid.

Solubility of the Monohydrate Form in Aqueous Media

|  | Duration (h) | Isolation Method | pH | Solubility (mg/mL) |
| --- | --- | --- | --- | --- |
| Sample 1 | 40 | 1 | 4.70 | 0.253 |
| Sample 2 | 138 | 1 | 4.09 | 0.259 |
| Sample 3 | 69 | 2 | 6.85 | 0.262 |

1 - Centrifuge 0.05 mL of sample at 15000 rpm for 30 minutes. Analyze supernatant.
2 - Centrifuge 0.5 mL of sample at 15000 rpm for 30 minutes. Analyze supernatant The solubility of the free base monohydrate form of Compound M also was determined in several aqueous media, as shown in the table, below. In all studies, excess solid of the compound was allowed to equilibrate at a temperature in the range of about 20 to 25° C. for 12-48 hours while stirring.

| Media | pH | Solubility (mg/mL) |
| --- | --- | --- |
| PBS | 6.9 | 0.18 |
| 0.01N HCl | 1.9 | 0.35 |
| FaSIF$^2$ | 6.8 | 0.44 |
| SGF$^3$ | 2.1 | 1.44 |

$^2$FaSIF is composed of 5 mM Na Taurocholate 1.5 mM Lecithin in 0.029M KH$_2$PO$_4$ 0.22M KCl pH 6.8
$^3$SGF is 0.25% (w/v) SDS 0.2% (w/v) NaCl in 0.01N HCl The solubility of the monohydrate form decreased slightly in presence of higher ionic strength (PBS), and increased to 0.35 mg/mL in the acidic hydrochloric acid solution. The solubility of the monohydrate form also increased significantly in the presence of surfactants (FaSIF and SGF). The aqueous solubility of the monohydrate form increased significantly when subjected to a pH less than one. For example, at pH 0.73 (adjusted with HCl), the solubility of the monohydrate form was 9.74 mg/mL and at pH 0.80, (adjusted with methane sulfonic acid), the solubility of the monohydrate form was 12.37 mg/mL.

Figure 13:
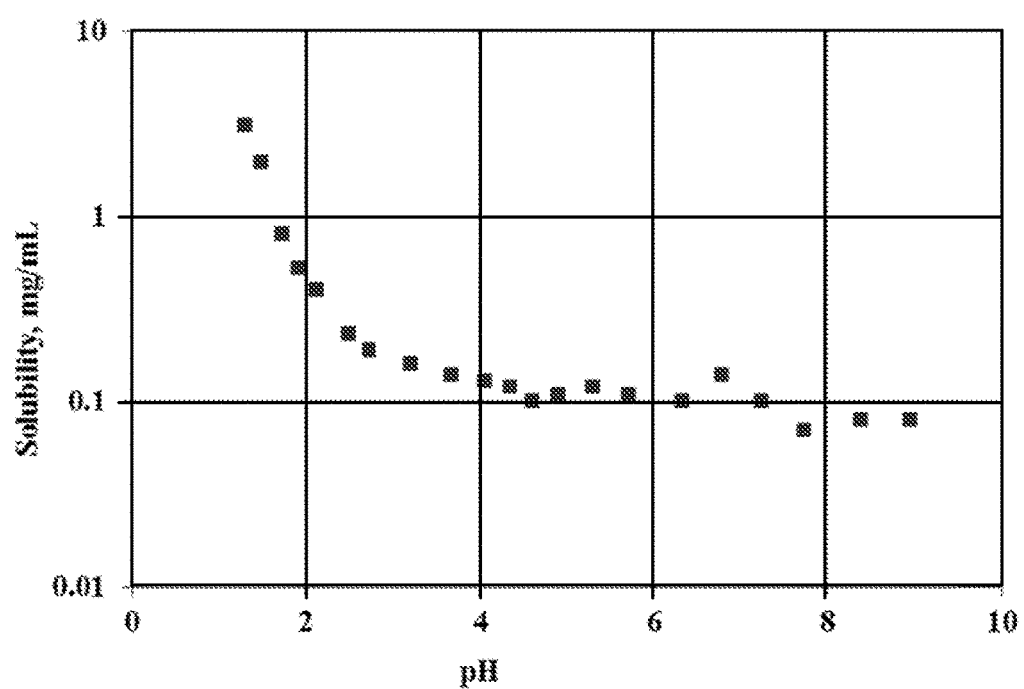
FIG. 13 depicts a pH-solubility profile of the free base monohydrate form of Compound M.

Example 2: pH-Solubility Profile of the Free Base Monohydrate Form of Compound M The pH-solubility profile (see FIG. 13) of the free base monohydrate form of Compound M was obtained in a universal buffer system containing 0.5 M phosphoric acid, acetic acid, boric acid, sodium hydroxide and sodium chloride in a pH range between 1.17 and 8.95. The experimental setup and analysis was performed using Symyx platform.

Example 3: Solubility of Select Free Base Forms of Compound M in Organic Solvents The solubility of the free base monohydrate form of Compound M in select organic solvents at a temperature in the range of about 20 to 25° C. was determined, as shown in the table, below. In all studies, excess solid of the compound was allowed to equilibrate for at least 12 hours while stirring.

Solubility of Monohydrate Form in Various Organic Solvents

| Solvent | Solubility, mg/mL | Polymorphic Form |
| --- | --- | --- |
| Methanol | 53.9 | monohydrate |
| Ethanol | 29.7 | monohydrate |
| Isopropanol | 8.80 | monohydrate |
| Acetonitrile | 127 | monohydrate (extra peak observed) |
| Ethyl Acetate | 20.1 | monohydrate |
| Methyl Ethyl Ketone | 45.8 | monohydrate + trace acetone solvate |
| 25% Dimethyl sulfoxide in water | 0.59 | monohydrate |
| 50% Dimethyl sulfoxide in water | 1.02 | monohydrate |
| 75% Dimethyl sulfoxide in water | 8.45 | monohydrate |
| Toluene | 1.90 | monohydrate |

Example 4: Photostability Studies of the Free Base Monohydrate and Amorphous Forms of Compound M When a solid powder sample of the free base monohydrate form of Compound A was exposed to photolytic conditions (1×ICH dose for UV and visible light), no chemical degradation of samples in amber glass vials was observed. As shown in the table below minimal degradation, 0.4% and 0.2%, was detected in samples in clear glass vials under UV and visible light, respectively.

Degradation of Solid Monohydrate Compound M After Exposure to UV-Vis Light

| | | Area % (215 nm) | | |
| --- | --- | --- | --- | --- |
| | | UV (200 W × h/m$^2$) | | Visible (1200 klux × h) |
| Peak | RRT | Amber | Clear | Amber | Clear |
| No MS signal | 0.80 | <0.01 | 0.02 | <0.01 | <0.01 |
| m/z 581 | 0.82 | <0.01 | 0.05 | <0.01 | <0.01 |

-continued

| | | Area % (215 nm) | | | |
|---|---|---|---|---|---|
| | | UV (200 W × h/m²) | | Visible (1200 klux × h) | |
| Peak | RRT | Amber | Clear | Amber | Clear |
| m/z 520 [M + Na]⁺ | 0.83 | <0.01 | 0.06 | <0.01 | <0.01 |
| m/z 390 | 0.84 | 0.06 | 0.19 | 0.05 | 0.13 |
| monohydrate | 1.00 | 99.89 | 99.64 | 99.89 | 99.83 |
| m/z 638 | 1.16 | 0.05 | 0.04 | 0.05 | 0.04 |
| Total Impurities | | 0.11 | 0.36 | 0.11 | 0.17 |
| % Recovery | | 101.4% | 99.7% | 100.9% | 99.6% |

Example 5: Solid State Stability of the Free Base Monohydrate Form of Compound M Solid samples of the free base monohydrate form of Compound M were placed under accelerated stability testing conditions (25° C./60% RH, 40° C./75% RH and 60° C./ambient RH) for 12 weeks. As shown in the table, below, no changes in solid state properties were observed.

Solid State Stability of the Monohydrate Form of Compound M—Accelerated Conditions

| | | | Week 2 | | | Week 4 | | | Week 8 | | | Week 12 | | |
|---|---|---|---|---|---|---|---|---|---|---|---|---|---|---|
| Peak | RRT | Initial | 25/60 | 40/75 | 60 C. | 25/60 | 40/75 | 60 C. | 25/60 | 40/75 | 60 C. | 25/60 | 40/75 | −20 C. |
| | | | | | | Area % (215 nm) | | | | | | | | |
| monohydrate | 1.00 | 100.0 | 99.18 | 99.35 | 99.21 | 99.90 | 99.86 | 99.90 | 99.97 | 99.92 | 99.97 | 100.0 | 100.0 | 100.0 |
| 2 | 1.09 | <0.1 | 0.27 | 0.31 | 0.25 | <0.1 | <0.1 | <0.1 | <0.1 | <0.1 | <0.1 | <0.1 | <0.1 | <0.1 |
| 3 | 1.25 | <0.1 | 0.28 | 0.35 | 0.27 | <0.1 | <0.1 | <0.1 | <0.1 | <0.1 | <0.1 | <0.1 | <0.1 | <0.1 |
| 4 | 1.53 | <0.1 | 0.28 | <0.1 | 0.27 | <0.1 | <0.1 | <0.1 | <0.1 | <0.1 | <0.1 | <0.1 | <0.1 | <0.1 |
| Total Impurities | | <0.1 | 0.82 | 0.65 | 0.79 | 0.01 | 0.14 | <0.1 | <0.1 | <0.1 | <0.1 | <0.1 | <0.1 | <0.1 |
| % API Recovery | | 100.2 | 100.3 | 100.8 | 100.4 | 100.8 | 100.6 | 101.0 | 101.1 | 101.1 | 100.9 | 100.0 | 100.2 | 99.5 |
| | | | | | | DSC, Dehydration | | | | | | | | |
| Onset, ° C. | | 45.4 | 48.0 | 48.9 | 44.2 | 46.1 | 45.0 | 47.7 | 55.3 | 48.8 | 47.1 | 46.7 | 48.6 | 45.1 |
| ΔH, J/g | | 96 | 118 | 121 | 80 | 111 | 110 | 109 | 103 | 101 | 104 | 104 | 109 | 90 |
| | | | | | | DSC, Melt | | | | | | | | |
| Onset, ° C. | | 152.5 | 152.5 | 152.8 | 152.5 | 152.5 | 152.9 | 152.5 | 152.4 | 152.4 | 152.0 | 152.4 | 152.5 | 151.7 |
| ΔH, J/g | | 71 | 70 | 69 | 73 | 69 | 70 | 71 | 70 | 69 | 70 | 70 | 77 | 74 |
| TGA, % Wt Loss | | 3.63 | 3.51 | 3.61 | 3.43 | 3.48 | 4.32 | 3.30 | 3.55 | 3.43 | 3.45 | 3.34 | 3.42 | 3.21 |

Example 6: Preparation of the Free Base Monohydrate Form of Compound M

The free base monohydrate form of Compound M can be formed in a variety of ways. For example, the free base monohydrate form of Compound M was formed by exposing a free base anhydrous I form of Compound M to a relative humidity above 15%. The free base monohydrate form of Compound M also was prepared by subjecting a free base anhydrous form of Compound M to 30% relative humidity, to result in a fully hydrated compound at 40% relative humidity, with a weight gain of 3.7 wt. %. As another example, the free base monohydrate form of Compound M was formed by preparing a slurry containing Compound M in acetonitrile/water through the anti-solvent addition of water, and then isolating the resulting compound.

Single crystals of the free base monohydrate form of Compound M were grown from acetone solution.

Example 7: Preparation of the Free Base Anhydrous I Form of Compound M

The free base anhydrous I form of Compound M can be formed in a variety of ways. For example, the free base anhydrous I form of Compound M was prepared by heating the free base monohydrate form of Compound M to 55° C. The free base anhydrous I form of Compound M also was prepared by subjecting the free base monohydrate form of Compound M to a relative humidity of less than 15%, at 25° C., The free base anhydrous I form of Compound M also was prepared by slurrying the free base monohydrate form of Compound M in propylene glycol at a concentration of about 14 mg/mL for at least 8 hours at a temperature in a range of 20° C. to 25° C., and isolating the solids by filtration. In another experiment, the free base anhydrous I form of Compound M was prepared by slurrying the free base monohydrate form of Compound M in PEG 400 at a concentration of about 14 mg/mL for at least 8 hours at a temperature in a range of 20° C. to 25° C., and isolating the solids by filtration Single crystals of the free base anhydrous I form of Compound M were grown by preparing a solution of Compound M in ethanol, and placing the solution in a desiccator with phosphorous pentoxide (20% relative humidity).

Example 8: Preparation of the Free Base Anhydrous II Form of Compound M

The free base anhydrous II form of Compound M can be formed in a variety of ways. For example, the free base anhydrous II form of Compound M was formed by desiccating a solid powder of the form of the acetone solvate form of Compound M, and rehydrating the desiccated solid at greater than 30% relative humidity. In another example, the free base anhydrous II form of Compound M was prepared by incubating the acetone solvate form of Compound M at a temperature in a range of 20° C. to 25° C. in a desiccator for up to eight months, and then storing the resulting product at at a temperature in a range of 20° C. to 25° C. and humidity in the range of about 20 to about 30% for 19 hours.

Example 9: Preparation of the Free Base Acetone Solvate Form of Compound M

The free base acetone solvate form of Compound M can be formed in a variety of ways. For example, the free base acetone solvate form of Compound M was prepared by slurrying the free base monohydrate form of Compound M with about 3.5 volumes of acetone for about 4 hours at a temperature in a range of 20° C. to 25° C., and then isolating the resulting solids by filtration.

Example 10: Preparation of the Free Base DMSO Hemisolvate Form of Compound M The free base DMSO hemisolvate form of Compound M can be formed in a variety of ways. For example, the free base DMSO hemisolvate form of Compound M was prepared by slurrying the free base monohydrate form of Compound M in 2.5 volumes of DMSO at a temperature in a range of 20° C. to 25° C. for 70 hours, and isolating the solids by filtration.

Single crystals of the free base DMSO hemisolvate form of Compound M were prepared by slow evaporation of a saturated DMSO solution.

Example 11: Preparation of the Free Base Amorphous Form of Compound M

The free base amorphous form of Compound M can be formed in a variety of ways. For example, the free base amorphous form of Compound M was formed by evaporating a crude reaction mixture of Compound M onto silica gel placed in tandem with the column (330 g REDISEP, well equilibrated) and purified via flash chromatography (10 minutes at 100% $CH_2Cl_2$, then 50 minutes of gradient from 0% to 5% of 1% ammonium hydroxide in methanol). The desired compound solution was collected and evaporated using rotary evaporator, yielding solids of the free base amorphous form of Compound M.

Example 12: Preparation of Co-Crystal Forms of Compound M

The co-crystal forms of Compound M were prepared by, for example, solution crystallization, cooling and evaporation, precipitation, or via a slurry of Compound M and the coformer in a solvent, such as ethanol/acetone, ethanol/ethyl acetate, acetone/acetic acid, isopropyl alcohol (IPA), acetonitrile, ethyl acetate, or ethanol.

The phosphoric acid co-crystal of Compound M was prepared by solution recrystallization using a 1:1 molar ratio of Compound M and phosphoric acid in ethanol/acetone The phosphoric acid co-crystal of Compound M also was prepared by solution crystallization using a 1:1 molar ratio of Compound M and phosphoric acid in acetone/acetic acid.

The maleic acid co-crystal of Compound M was prepared by slurry crystallization using a 1:1 molar ratio of Compound M and anhydrous maleic acid in IPA.

The succinic acid co-crystal of Compound M was prepared by cooling and evaporation using a 2:1 molar ratio of Compound M and anhydrous succinic acid in IPA, or a 2:1 molar ratio of Compound M and anhydrous succinic acid in acetonitrile, or a 2:1 molar ratio of Compound M and anhydrous succinic acid in ethanol.

The sorbic acid co-crystal of Compound M was prepared by evaporation using a 2:1 molar ratio of Compound M and anhydrous sorbic acid in ethanol.

The glutaric acid co-crystal of Compound M was prepared by cooling and evaporation using a 2:1 molar ratio of Compound M and anhydrous glutaric acid in ethanol.

The urea co-crystal of Compound M was prepared by adding Compound M to a solution of urea in ethanol using 4:1 molar ratio of Compound M and anhydrous urea, followed by slow crystallization of the co-crystal form.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A free base form of 6-{(1R)-1-[8-fluoro-6-(1-methyl-1H-pyrazol-4-yl)[1,2,4]triazolo[4,3-a]pyridin-3-yl]ethyl}-3-(2-methoxyethoxy)-1,6-naphthyridin-5(6H)-one, wherein the free base form is a monohydrate form.

2. The free base form of claim 1, wherein the monohydrate form is crystalline.

3. The free base form of claim 1, wherein the monohydrate form is characterized by an X-ray powder diffraction pattern comprising peaks at about 6.6, 7.9, 14.5, 15.1, 15.8 and 22.2±0.2° 2θ using Cu Kα radiation.

* * * * *